US012632790B1

(12) United States Patent

Dey et al.

(10) Patent No.: US 12,632,790 B1
(45) Date of Patent: May 19, 2026

(54) SYSTEMS AND METHODS FOR A CLOUD-BASED DATA PLATFORM FOR SCIENTIFIC AND BIOMEDICAL RESEARCH

(71) Applicant: Manifold, Inc., San Francisco, CA (US)

(72) Inventors: Sourav Dey, San Francisco, CA (US); Jakov Kucan, Cambridge, MA (US); John Maynard, Acton, MA (US); Catherine Pierson, Wayland, MA (US); Vinay Seth Mohta, Newton, MA (US)

(73) Assignee: MANIFOLD, INC., Newton, MA (US)

( * ) Notice: Subject to any disclaimer, the term of this patent is extended or adjusted under 35 U.S.C. 154(b) by 151 days.

(21) Appl. No.: 18/359,743

(22) Filed: Jul. 26, 2023

Related U.S. Application Data

(60) Provisional application No. 63/506,552, filed on Jun. 6, 2023, provisional application No. 63/392,820, filed on Jul. 27, 2022.

(51) Int. Cl.
    *G06N 20/00* (2019.01)
    *G16H 15/00* (2018.01)
    *G16H 10/60* (2018.01)

(52) U.S. Cl.
    CPC ............. *G06N 20/00* (2019.01); *G16H 15/00* (2018.01); *G16H 10/60* (2018.01)

(58) Field of Classification Search
    None
    See application file for complete search history.

(56) References Cited

U.S. PATENT DOCUMENTS

| | | | | |
|---|---|---|---|---|
| 9,672,279 | B1 * | 6/2017 | Cohen | G06F 16/35 |
| 10,665,348 | B1 * | 5/2020 | Krayer | G16H 50/30 |
| 11,102,304 | B1 * | 8/2021 | Jain | H04L 67/12 |
| 2017/0039341 | A1 * | 2/2017 | Shklarski | G16H 50/70 |
| 2018/0039731 | A1 * | 2/2018 | Szeto | G16H 40/20 |
| 2019/0304575 | A1 * | 10/2019 | Beltre | G16H 40/20 |
| 2020/0381087 | A1 * | 12/2020 | Ozeran | G06F 16/31 |
| 2021/0090694 | A1 * | 3/2021 | Colley | G16H 50/50 |
| 2021/0286604 | A1 * | 9/2021 | Peccoud | G06F 8/35 |
| 2022/0044812 | A1 * | 2/2022 | Barnes | G16H 50/20 |
| 2022/0068482 | A1 * | 3/2022 | Zimmerman | G16H 70/20 |
| 2022/0083605 | A1 * | 3/2022 | Duishoev | G06N 5/02 |
| 2022/0093271 | A1 * | 3/2022 | Huang | G06N 7/01 |
| 2022/0114490 | A1 * | 4/2022 | Das | G06N 3/088 |
| 2022/0189635 | A1 * | 6/2022 | Gopalakrishnan | G16H 10/60 |
| 2022/0215948 | A1 * | 7/2022 | Bardot | G16H 40/40 |
| 2022/0375560 | A1 * | 11/2022 | Bonageri | G06N 20/00 |

OTHER PUBLICATIONS

Vaishali A. Ingle, Processing of Unstructured data for Information Extraction, 2012 Nirma University International Conference on Engineering, NUICONE—2012, Dec. 6-8, 2012.*

* cited by examiner

*Primary Examiner* — David J Stoltenberg
(74) *Attorney, Agent, or Firm* — Haynes and Boone, LLP

(57) ABSTRACT

Embodiments described herein provide a data cloud platform that facilitates an end-to-end workflow for scientific and biomedical research, such that scientists and researchers may have easy access to scientific and biomedical data.

20 Claims, 21 Drawing Sheets

500

Receive, via a data interface, unstructured data from one or more medical data sources 502

Convert the unstructured data into a plurality of data samples associated with a set of data attributes according to a pre-defined format 504

Formulate a training dataset by grouping the plurality of data samples based on past research results 506

Generate, by a machine learning engine, predicted research finding availability based on availability of the set of data attributes in the training dataset 508

Train the machine learning engine based on a training objective that is computed by comparing the predicted research finding availability and the past research results 510

Generate, by the trained machine learning engine, a prediction of research findings based on availability of the plurality of data samples in response to research data queries 512

310

Patient Portal 331

Query Interface 332

Data Catalog 333

Proposal Intake 334

Computational Lab 335

Research Control 336

Research Search 337

Data Warehouse 319

Participant CRM 341

Targeted Outreach 342

Data Access Control 354

Metadata Management 355

Transformation 351

Standardization 352

Ingestion 353

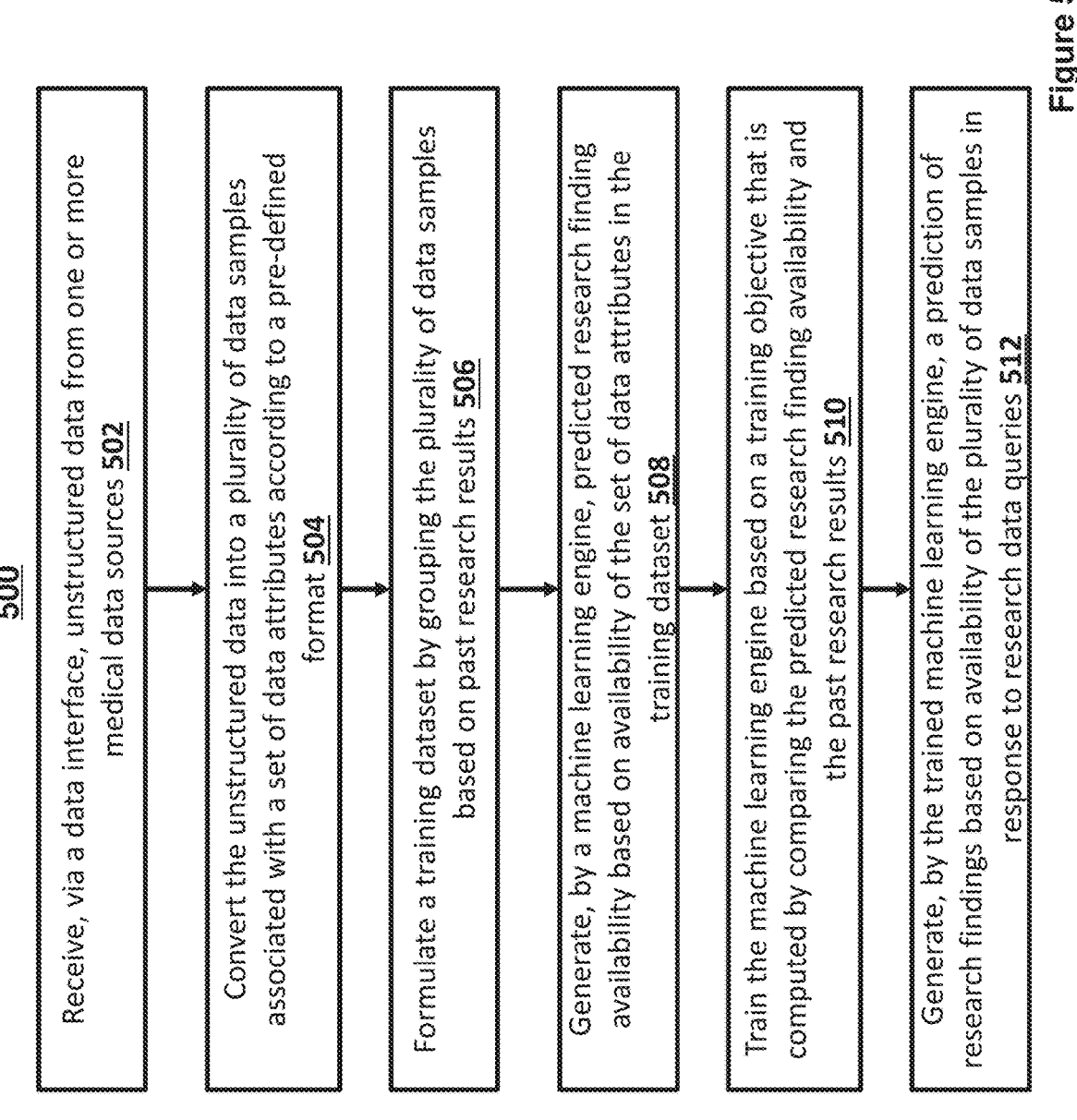

500

Receive, via a data interface, unstructured data from one or more medical data sources 502

Convert the unstructured data into a plurality of data samples associated with a set of data attributes according to a pre-defined format 504

Formulate a training dataset by grouping the plurality of data samples based on past research results 506

Generate, by a machine learning engine, predicted research finding availability based on availability of the set of data attributes in the training dataset 508

Train the machine learning engine based on a training objective that is computed by comparing the predicted research finding availability and the past research results 510

Generate, by the trained machine learning engine, a prediction of research findings based on availability of the plurality of data samples in response to research data queries 512

Figure 5

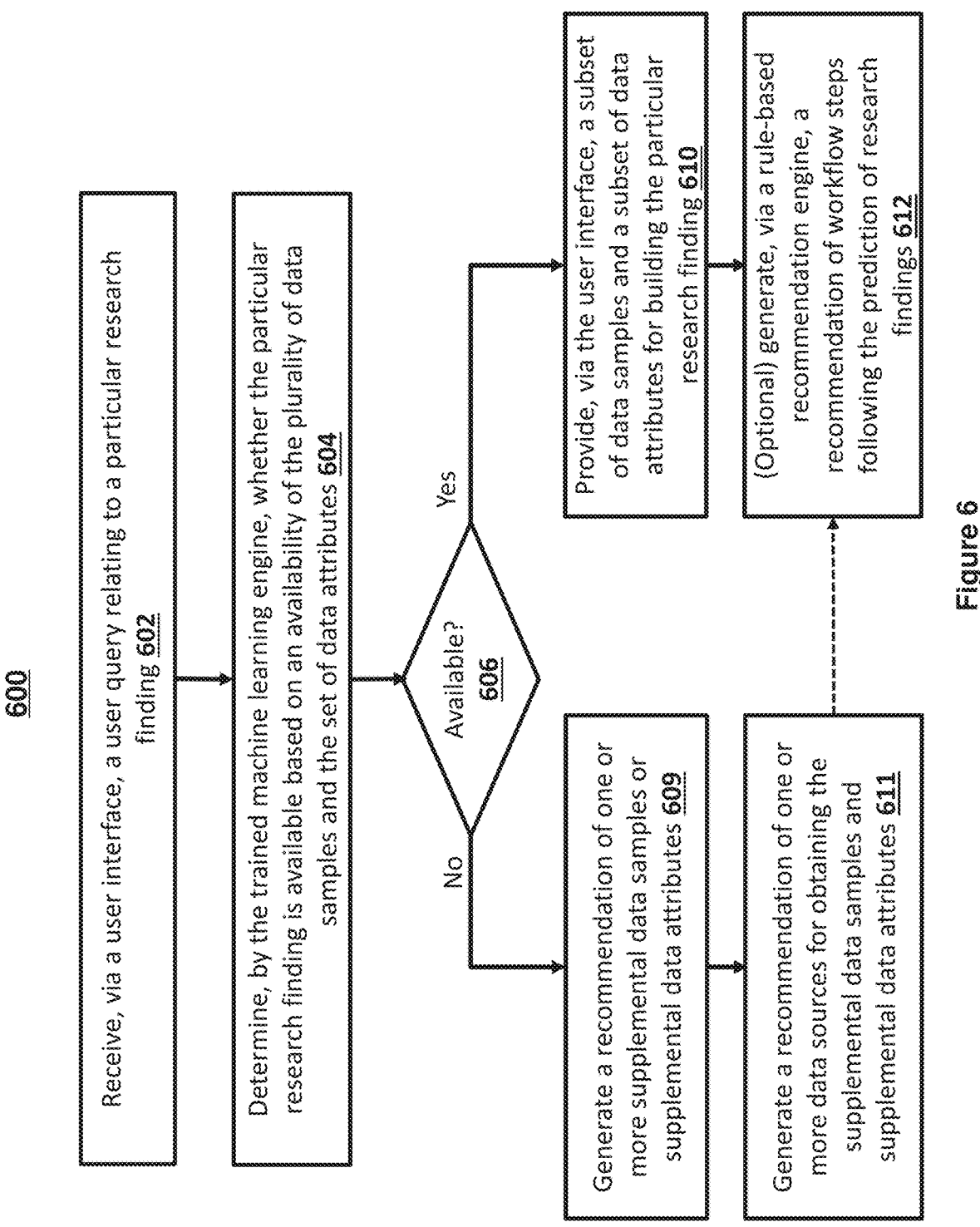

600

Receive, via a user interface, a user query relating to a particular research finding 602

Determine, by the trained machine learning engine, whether the particular research finding is available based on an availability of the plurality of data samples and the set of data attributes 604

Available? 606

Yes

No

Provide, via the user interface, a subset of data samples and a subset of data attributes for building the particular research finding 610

(Optional) generate, via a rule-based recommendation engine, a recommendation of workflow steps following the prediction of research findings 612

Generate a recommendation of one or more supplemental data samples or supplemental data attributes 609

Generate a recommendation of one or more data sources for obtaining the supplemental data samples and supplemental data attributes 611

Figure 6

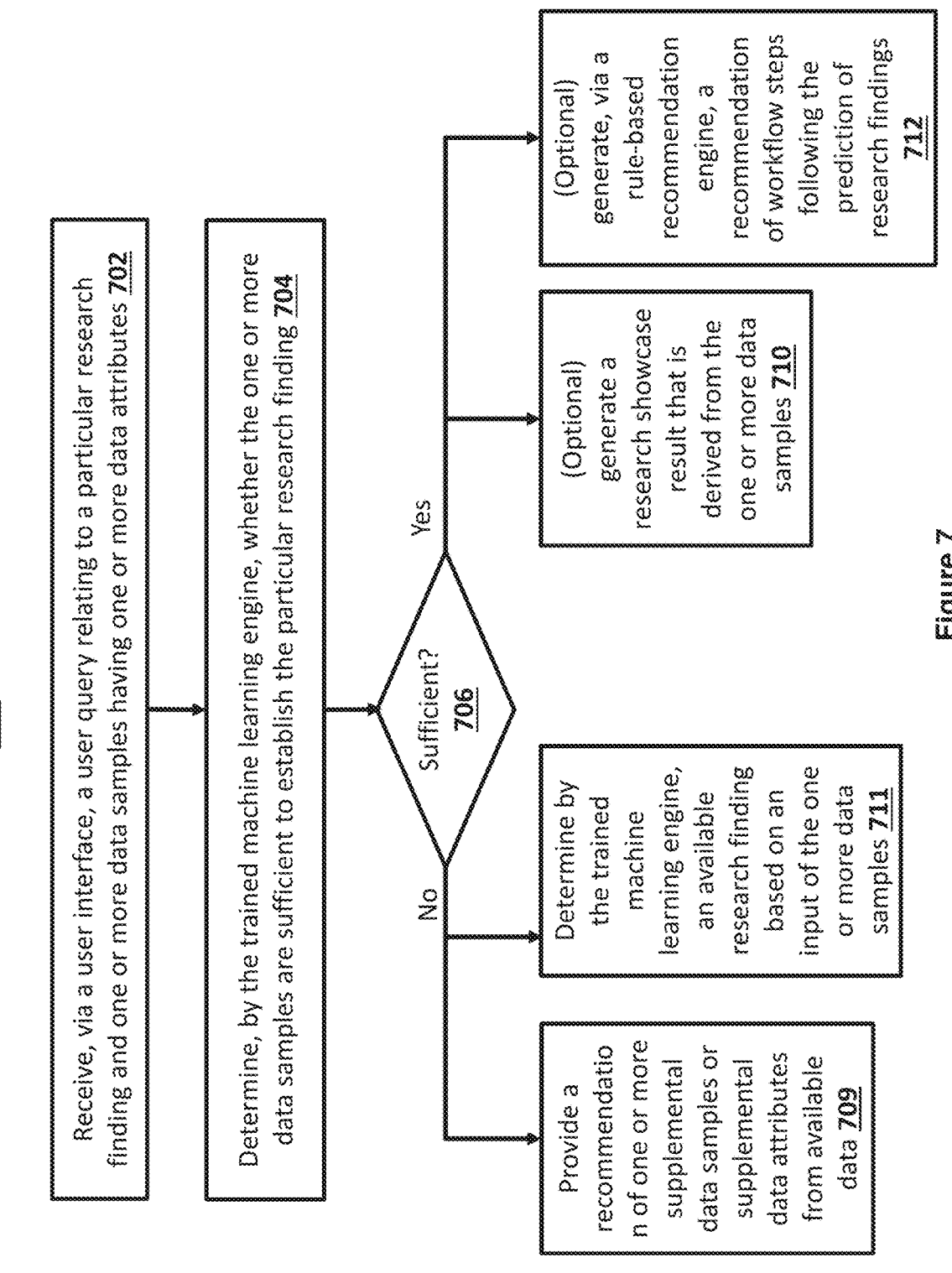

700

Receive, via a user interface, a user query relating to a particular research finding and one or more data samples having one or more data attributes 702

Determine, by the trained machine learning engine, whether the one or more data samples are sufficient to establish the particular research finding 704

Sufficient? 706

Yes

No (Optional) generate a research showcase result that is derived from the one or more data samples 710

(Optional) generate, via a rule-based recommendation engine, a recommendation of workflow steps following the prediction of research findings 712

Determine by the trained machine learning engine, an available research finding based on an input of the one or more data samples 711

Provide a recommendation of one or more supplemental data samples or supplemental data attributes from available data 709

Figure 8C:
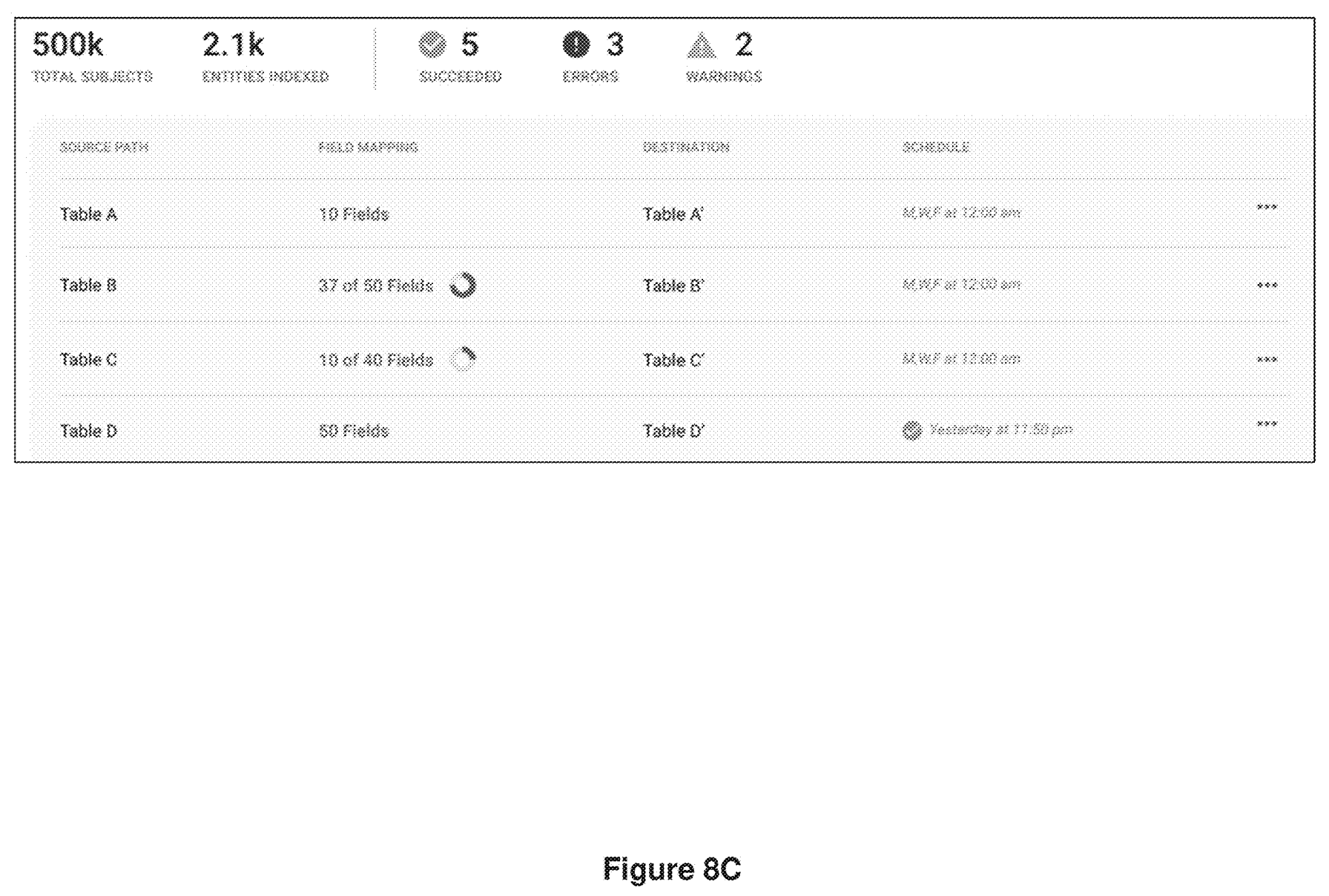

500k TOTAL SUBJECTS

2.1k ENTRIES INDEXED

5 SUCCEEDED

3 ERRORS

2 WARNINGS

| SOURCE PATH | FIELD MAPPING | DESTINATION | SCHEDULE |
|---|---|---|---|
| Table A | 10 Fields | Table A | daily at 12:00 am |
| Table B | 37 of 50 Fields | Table B | daily at 12:00 am |
| Table C | 10 of 40 Fields | Table C | daily at 12:00 am |
| Table D | 50 Fields | Table D | Yesterday at 11:00 pm |

Figure 8F:
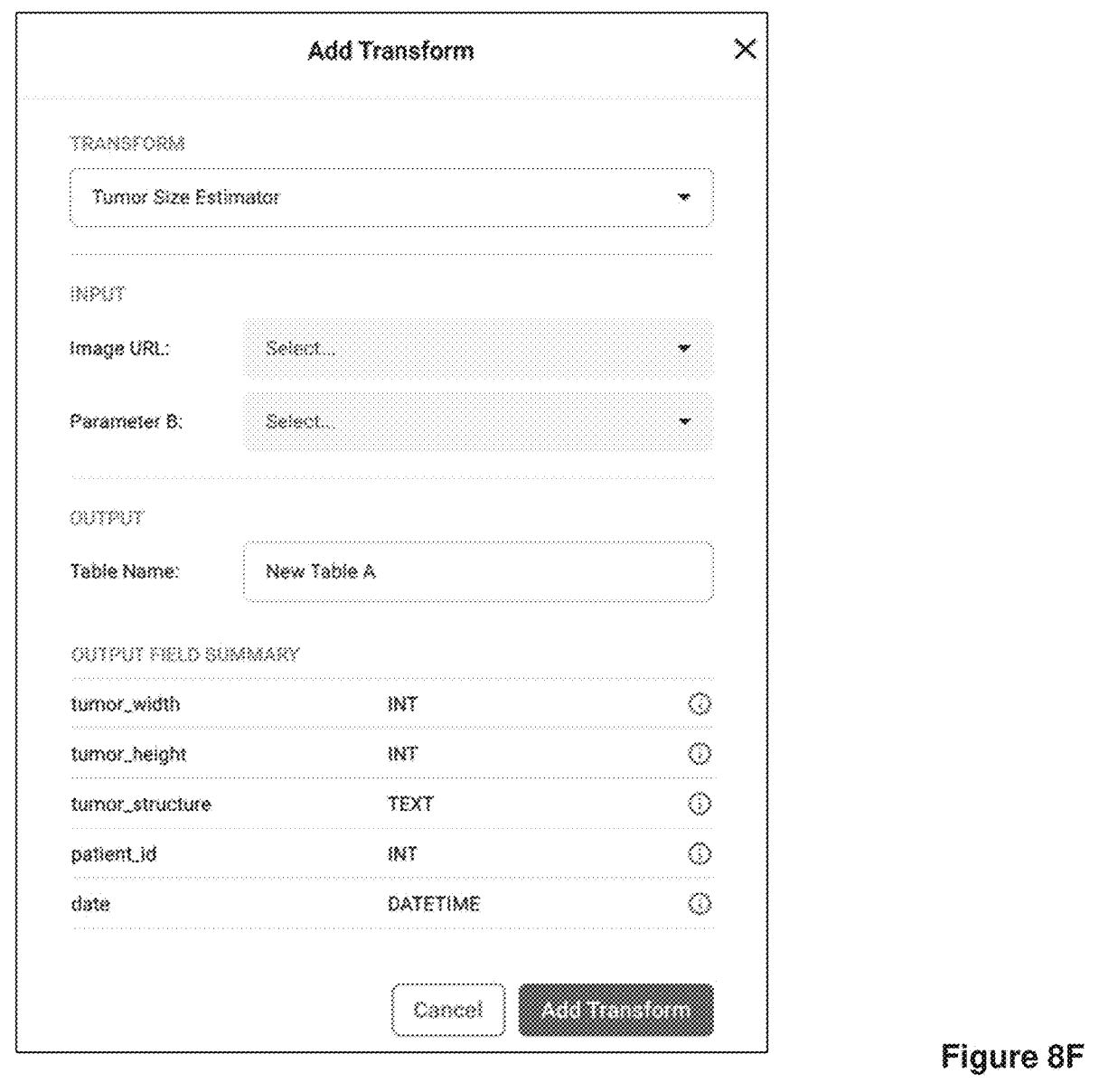

Add Transform

×

TRANSFORM

Tumor Size Estimator ▾

INPUT

Image URL : Select... ▾

Parameter B: Select... ▾

OUTPUT

Table Name: New Table A

OUTPUT FIELD SUMMARY

| tumor_width | INT |
| tumor_height | INT |
| tumor_structure | TEXT |
| patient_id | INT |
| date | DATETIME |

Cancel Add Transform

Project Arugula

PROJECT HISTORY

Dolores suscipit et. Voluptatem consequatur assumenda alias quos. Reprehenderit minus consectetur aut est. Esse natus provident et facere omnis accusantium accusamus corporis.

PROPOSAL ACCEPTANCE

Asperiores aut voluptas consequatur accusamus laborum similique. A eos aut qui sapiente quia delectus. Consectetur ea est officiis ex quidem. Quisquam qui pariatur id voluptas rerum aliquid. Veniam explicabo facilis aut porro.

*Accepted on 2030-01-01 by Aaron Aardvark*

IRB APPROVAL

*Approved on 2030-01-01 by Aaron Aardvark*

DATA REVIEW

Quis aut aut. Dolorum dicta sapiente. Ipsa vero inventore voluptatem animi dolores praesentium. Nemo non tenetur.

*Reviewed on 2030-01-01 by Aaron Aardvark*

ANALYSIS VERIFICATION

Quis aut aut. Dolorum dicta sapiente. Ipsa vero inventore voluptatem animi dolores praesentium. Nemo non tenetur.

PUBLISH

Quis aut aut. Dolorum dicta sapiente. Ipsa vero inventore voluptatem animi dolores praesentium. Nemo non tenetur.

SYSTEMS AND METHODS FOR A CLOUD-BASED DATA PLATFORM FOR SCIENTIFIC AND BIOMEDICAL RESEARCH

CROSS REFERENCE

The application claims priority under 35 U.S.C. 119 to and commonly-owned U.S. Provisional Application Nos. 63/392,820, filed Jul. 27, 2022, and 63/506,552, filed Jun. 6, 2023, both of which are hereby expressly incorporated by reference herein in their entirety.

TECHNICAL FIELD

The embodiments relate generally to a data cloud platform for scientific and biomedical research.

BACKGROUND

Large scale longitudinal studies are expensive to set up and operate because of the challenges associated with recruiting participants and the manual work required to gather biological samples and data, measure attributes about the participants, and collect survey responses from the participants. In addition, there is a vast amount of data from such studies that must be ingested and processed in order to be usable by researchers for scientific or biomedical research, including discovery of new causes or treatment of diseases. The data can have multiple modalities such as cell or tissue samples, wearable device data, electronic health records, whole genome sequencing, whole exome sequencing, single nucleotide-polymorphism (SNP) genotyping, epigenomics, transcriptomics, and metabolomics.

Therefore, there is a need for a data platform to facilitate end-to-end workflow from data collection to research collaboration.

BRIEF DESCRIPTION OF THE DRAWINGS

FIG. 5 is an example logic flow diagram illustrating a method of data integration for managing research project workflow dynamics based on the data cloud platform shown in FIGS. 1-2B and FIGS. 3A-4, according to some embodiments described herein.

FIG. 6 is an example logic flow diagram illustrating a method of responding to a user query relation to a research topic, according to some embodiments described herein.

FIG. 7 is an example logic flow diagram illustrating an alternative embodiment of responding to a user query relation to a research topic, according to some embodiments described herein.

FIGS. 8A-8G provide various example user interface (UI) diagrams of the data cloud platform shown in FIGS. 1-4, according to embodiments described herein.

FIGS. 9A-9E provide additional user interface (UI) diagrams of the data cloud platform shown in FIGS. 1-4, according to embodiments described herein.

Figure 1:
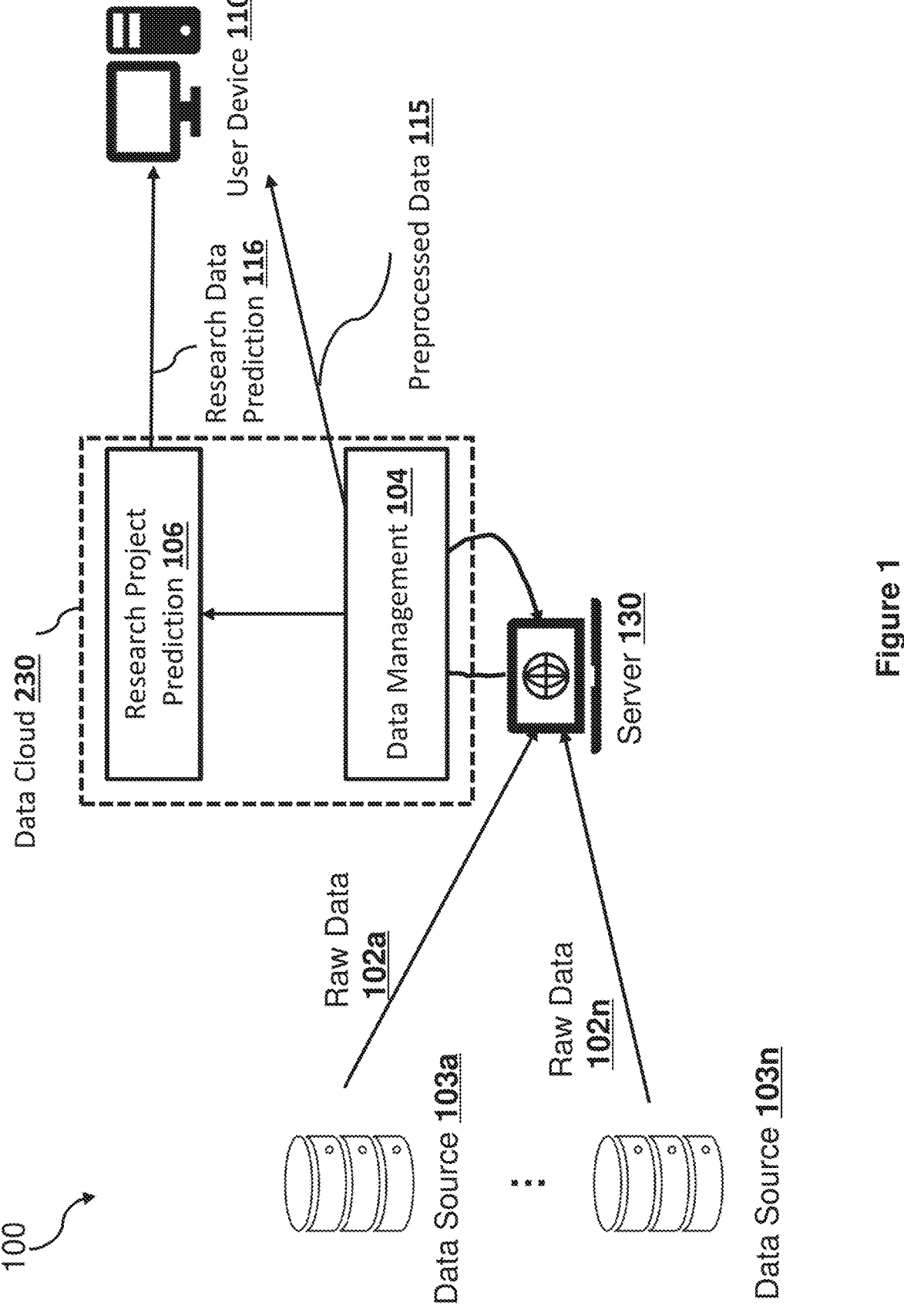
FIG. 1 is an example data flow diagram illustrating an overview of interactions between the server hosting the data cloud platform and various affiliated entities, according to embodiments described herein.

Embodiments of the disclosure and their advantages are best understood by referring to the detailed description that follows. It should be appreciated that like reference numerals are used to identify like elements illustrated in one or more of the figures, wherein showings therein are for purposes of illustrating embodiments of the disclosure and not for purposes of limiting the same.

DETAILED DESCRIPTION

As used herein, the term "network" may comprise any hardware or software-based framework that includes any artificial intelligence network or system, neural network or system and/or any training or learning models implemented thereon or therewith.

As used herein, the term "module" may comprise a hardware or software-based framework that performs one or more functions. In some embodiments, the module may be implemented on one or more neural networks.

In a typical research environment, research data collection may not be efficient, e.g., outreach and follow-up with participants may not be targeted, and often require manual consent management. Other common issues include data consistency issues from sharded record keeping, repetitive registry linkages, manual process (e.g., defining sub-studies, etc.), and participants not usually having a way to interact directly with the study and their data. Data management for a large amount of records can also be challenging, e.g., data is siloed in various files, formats, and systems; data discovery is a long process with many back and forth emails; data access is too restrictive for learning about data and, at the same time, not restrictive enough for sharing data with collaborators; common, useful data transformations are done over and over again; data is not standardized so it is hard to harmonize across studies, and/or the like. As a result, for scientists and researchers conducting the research, external collaboration is difficult without violating data usage policies, e.g., access to data without taking it out of the protected environment. It can also be difficult for researchers to set up cloud computing environments with access to high performance computing resources using best-practices, or to leverage previous work, e.g., useful data transformations, known caveats, unsuccessful analyses. Therefore, it is generally hard to collaborate on iterative computational analyses with all its context.

In view of the need for a data platform aggregating scientific data for researchers such that scientists and researchers may have easy access to scientific and clinical data, embodiments described herein provide a data cloud platform to facilitate an end-to-end research workflow from data collection to research collaboration, including purpose-built applications for researchers.

It is noted that although FIGS. 1-8F are provided for embodiments of scientific and biomedical research, embodiments of the data cloud platform described herein may be applied to any type of data-based research and analytics such as market research, system anomaly research, code program research, and/or the like.

System Overview

FIG. 1 is an example data flow diagram 100 illustrating an overview of interactions between the server hosting the data cloud platform and various affiliated entities, according to embodiments described herein. The data cloud platform 230 may be implemented at a server 130, which may receive raw data 102a-n from one or more data sources 103a-n. It is noted that the data sources 103a-n are for illustrative purpose only, and any number of data sources may be engaged with the data cloud platform implemented at server 130.

For example, the data sources 103a-n may comprise any of research institute, survey service servers, hospitals, clinics, web-based patient portals, user health tracker mobile applications, and/or the like. Raw research data 102a-n may comprise various unstructured data such as patient records, survey records, radiology images, clinical registries, gene sequencing data, histology images, academic publications, clinical trial management system (CTMS) reports, and/or the like.

A data management module 104 at the server 130 may convert such raw research data 102a-n into preprocessed data 115 in a pre-defined format ready for research use. For example, the preprocessed data 115 may take a form of standardized spreadsheets having a number of rows representing different individual cases (patients) and a number of columns representing different case (patient) attributes such as patient name, age, residence, zip code, smoke history, medicine history, pre-existing condition, symptoms and dates, diagnoses, and/or the like.

In one embodiment, the data cloud platform 230 may further comprise a research project prediction module 106. The prediction module 106 may engage a machine learning engine that is trained based on the standardized research data fields and prior research results to predict whether a particular research topic may be achievable based on available datasets. For example, the machine learning engine may predict whether a research topic of "correlation between blood sugar level and breast cancer" can be established using a dataset of 500 female patient records between age 40-50 including monthly blood sugar results and annual mammogram results.

In some implementations, the research topic may comprise a correlation or a causality between a first data attribute and a second data attribute. Establishing causality between data attributes may have a higher data requirement than to establish correlation only. Therefore, the data cloud platform 230 sometimes may determine a research topic relating to causality between certain data attributes is unachievable based on available data, even if correlation between the same data attributes may be achievable.

In one embodiment, if the machine learning engine generates a prediction 116 that the available dataset is insufficient to achieve the desired research topic, the machine learning engine may further suggest additional data that may supplement the existing available research data. In the above example, the machine learning engine may predict that the mere data of 500 female patient records between age 40-50 are insufficient and may suggest additional datasets such as patient records at different age groups, and additional medial history of each patient.

In one embodiment, a user (e.g., scientist, researcher, etc.) may operate the user device 110 to receive the research data prediction 116 and/or the preprocessed data 115 and interact with the data cloud platform 230, which is implemented at the remote server 130, to submit a query, upload datasets, and/or the like. For example, FIGS. 8A-8F provide example user interface on a user device 110 for a user to view and manage research projects and data attributes needed for the respective research project.

In this way, bio-medical research may be streamlined by AI-assisted easy data access. Research efficiency can thus be improved by the cloud-based data platform.

Computer and Network Environment

Figure 2A:
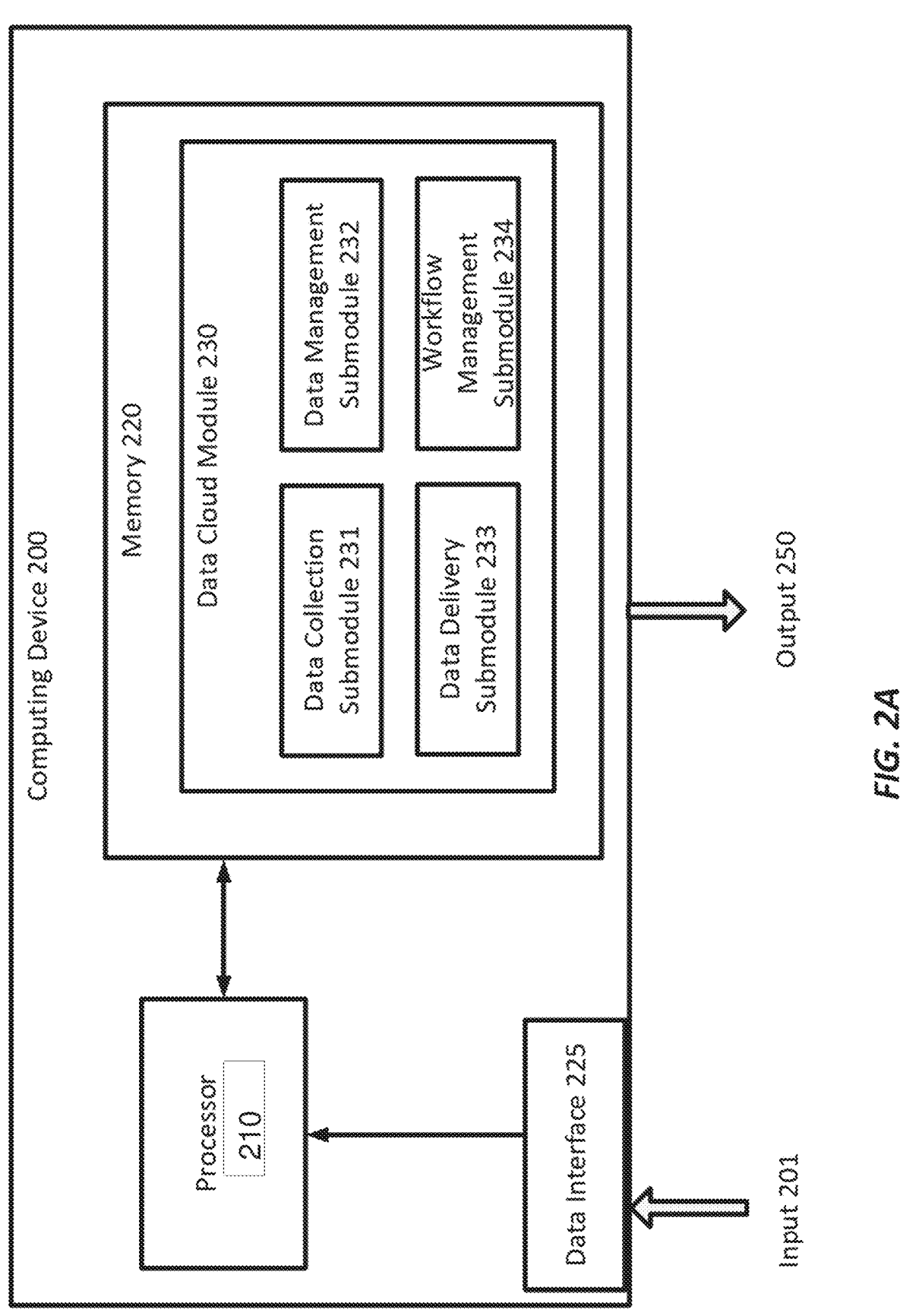
FIG. 2A is a simplified diagram illustrating a computing device implementing the cloud-based data platform, according to one embodiment described herein.

FIG. 2A is a simplified diagram illustrating a computing device 200 implementing the cloud-based data platform, according to one embodiment described herein. In some embodiments, the server 130 shown in FIG. 1 may be implemented at the computing device 200. As shown in FIG. 2, computing device 200 includes a processor 210 coupled to memory 220. Operation of computing device 200 is controlled by processor 210. And although computing device 200 is shown with only one processor 210, it is understood that processor 210 may be representative of one or more central processing units, multi-core processors, microprocessors, microcontrollers, digital signal processors, field programmable gate arrays (FPGAs), application specific integrated circuits (ASICs), graphics processing units (GPUs) and/or the like in computing device 200. Computing device 200 may be implemented as a stand-alone subsystem, as a board added to a computing device, and/or as a virtual machine.

Memory 220 may be used to store software executed by computing device 200 and/or one or more data structures used during operation of computing device 200. Memory 220 may include one or more types of machine-readable media. Some common forms of machine-readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip, or cartridge, and/or any other medium from which a processor or computer is adapted to read.

Processor 210 and/or memory 220 may be arranged in any suitable physical arrangement. In some embodiments, processor 210 and/or memory 220 may be implemented on a same board, in a same package (e.g., system-in-package), on a same chip (e.g., system-on-chip), and/or the like. In some embodiments, processor 210 and/or memory 220 may include distributed, virtualized, and/or containerized computing resources. Consistent with such embodiments, processor 210 and/or memory 220 may be located in one or more data centers and/or cloud computing facilities.

In some examples, memory 220 may include non-transitory, tangible, machine readable media that includes executable code that when run by one or more processors (e.g., processor 210) may cause the one or more processors to perform the methods described in further detail herein. For example, as shown, memory 220 includes instructions for the data cloud module 230 that may be used to implement and/or emulate the systems and models, and/or to implement any of the methods described further herein. A data cloud module 230 may receive input 240 such as raw input clinical data via the data interface 215 and generate an output 250 which may be workflow data.

The data interface 225 may comprise a communication interface, a user interface (such as a voice input interface, a graphical user interface, and/or the like). For example, the computing device 200 may receive the input 240 (such as a training dataset) from a networked database via a communication interface (e.g., network interface 243 in FIG. 2B). Or the computing device 200 may receive the input 201 such as raw clinical data, from a user via the user interface.

In some embodiments, the data cloud module 230 is configured to provide easy data access and workflow management for scientists and researchers. The data cloud module 230 may further include a data collection submodule 231, a data management submodule 232, a data delivery submodule 233, and a workflow management submodule 234, and/or other submodules. In one embodiment, the data cloud module 230 and its submodules 231-234 may be implemented by hardware, software and/or a combination thereof.

For example, the data collection submodule 231 may provide a data pipeline for A/B testing, integration with data generation systems i.e., biospecimens, tumor registries, imaging, EMR, omics, etc. The data management submodule 232 may provide a data steward application and/or a data exploration application to provide purpose-built user interfaces for data warehousing, data pipeline management, and metadata-advanced search and query, fine-grained access control, large pre-installed transformer libraries, AI-enabled data standardization, and flexibility to develop custom transformers. The data delivery submodule 233 may provide a client portal application that hosts a user interface for delivering datasets or research results to a user. The data delivery submodule 233 may further provide a participant management application that hosts a participant portal on a user device to provide simplified digital consent management, AI-assisted registry linkage, AI-assisted workflows to improve participant engagement. The workflow management submodule 234 may provide a research workflow application and/or compute notebook application that manages a research project and provides a version control system for research workflow, workflow built for various common collaboration patterns, from proposal review to data reviews, cloud-hosted one-click development environments, e.g., Jupyter, R, SAS and searchable library of previous research.

Some examples of computing devices, such as computing device 200 may include non-transitory, tangible, machine readable media that include executable code that when run by one or more processors (e.g., processor 210) may cause the one or more processors to perform the processes of method. Some common forms of machine-readable media that may include the processes of method are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Figure 2B:
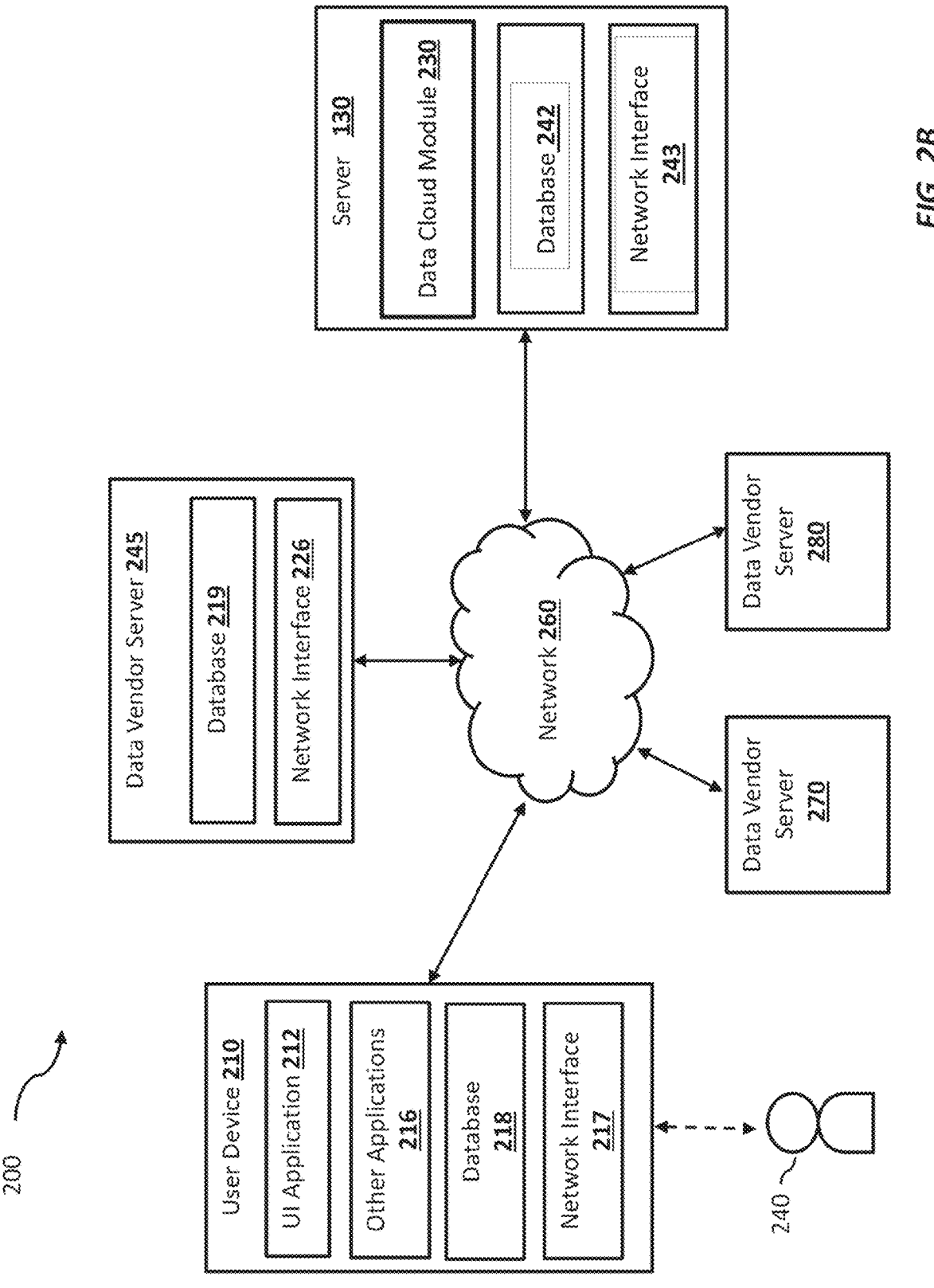
FIG. 2B is a simplified block diagram of a networked system suitable for implementing the data cloud framework described in FIG. 1, according to one embodiment described herein.

FIG. 2B is a simplified block diagram of a networked system suitable for implementing the data cloud framework described in FIG. 1, and other embodiments described herein. In one embodiment, block diagram 200 shows a system including the user device 210 which may be operated by user 240, data vendor servers 245, 270 and 280, server 130, and other forms of devices, servers, and/or software components that operate to perform various methodologies in accordance with the described embodiments. Exemplary devices and servers may include device, stand-alone, and enterprise-class servers which may be similar to the computing device 200 described in FIG. 2A, operating an OS such as a MICROSOFT® OS, a UNIX® OS, a LINUX® OS, or other suitable device and/or server-based OS. It can be appreciated that the devices and/or servers illustrated in FIG. 1 may be deployed in other ways and that the operations performed, and/or the services provided by such devices and/or servers may be combined or separated for a given embodiment and may be performed by a greater number or fewer number of devices and/or servers. One or more devices and/or servers may be operated and/or maintained by the same or different entities.

The user device 210, data vendor servers 245, 270 and 280, and the server 230 may communicate with each other over a network 260. User device 210 may be utilized by a user 240 (e.g., a driver, a system admin, and/or various participants that interact with data cloud platform 310 shown in FIG. 3A, etc.) to access the various features available for user device 210, which may include processes and/or applications associated with the server 230 to receive an output data anomaly report.

User device 210, data vendor server 245, and the server 230 may each include one or more processors, memories, and other appropriate components for executing instructions such as program code and/or data stored on one or more computer readable mediums to implement the various applications, data, and steps described herein. For example, such instructions may be stored in one or more computer readable media such as memories or data storage devices internal and/or external to various components of system 200, and/or accessible over network 260.

User device 210 may be implemented as a communication device that may utilize appropriate hardware and software configured for wired and/or wireless communication with data vendor server 245 and/or the server 230. For example, in one embodiment, user device 210 may be implemented as an autonomous driving vehicle, a personal computer (PC), a smart phone, laptop/tablet computer, wristwatch with appropriate computer hardware resources, eyeglasses with appropriate computer hardware (e.g., GOOGLE GLASS®), other type of wearable computing device, implantable communication devices, and/or other types of computing devices capable of transmitting and/or receiving data, such as an IPAD® from APPLE®. Although only one communication device is shown, a plurality of communication devices may function similarly for one or multiple users.

User device 210 of FIGS. 2A-2B contains a user interface (UI) application 212, and/or other applications 216, which may correspond to executable processes, procedures, and/or applications with associated hardware. For example, the user device 210 may receive a message indicating a biomedical record from the server 230 and display the message via the UI application 212. In other embodiments, user device 210 may include additional or different modules having specialized hardware and/or software as required.

In various embodiments, user device 210 includes other applications 216 as may be desired in particular embodiments to provide features to user device 210. For example, other applications 216 may include security applications for implementing client-side security features, programmatic client applications for interfacing with appropriate application programming interfaces (APIs) over network 260, or other types of applications. Other applications 216 may also include communication applications, such as email, texting, voice, social networking, and IM applications that allow a user to send and receive emails, calls, texts, and other notifications through network 260. For example, the other application 216 may be an email or instant messaging application that receives a prediction result message from the server 230. Other applications 216 may include device interfaces and other display modules that may receive input and/or output information. For example, other applications 216 may contain software programs for asset management, executable by a processor, including a graphical user interface (GUI) configured to provide an interface to the user 240 to view requested biomedical data.

User device 210 may further include database 218 stored in a transitory and/or non-transitory memory of user device 210, which may store various applications and data and be utilized during execution of various modules of user device 210. Database 218 may store user profile relating to the user 240, predictions previously viewed or saved by the user 240, historical data received from the server 230, and/or the like. In some embodiments, database 218 may be local to user device 210. However, in other embodiments, database 218 may be external to user device 210 and accessible by user device 210, including cloud storage systems and/or databases that are accessible over network 260.

User device 210 includes at least one network interface component 217 adapted to communicate with data vendor server 245 and/or the server 230. In various embodiments, network interface component 219 may include a DSL (e.g., Digital Subscriber Line) modem, a PSTN (Public Switched Telephone Network) modem, an Ethernet device, a broadband device, a satellite device and/or various other types of wired and/or wireless network communication devices including microwave, radio frequency, infrared, Bluetooth, and near field communication devices.

Data vendor server 245 may correspond to a server that hosts one or more of the databases in data sources 103*a-n* (or collectively referred to as 203) to provide training datasets including biomedical data to the server 230. The data source may comprise database 219 that may be implemented by one or more relational database, distributed databases, cloud databases, and/or the like.

The data vendor server 245 includes at least one network interface component 226 adapted to communicate with user device 210 and/or the server 230. In various embodiments, network interface component 226 may include a DSL (e.g., Digital Subscriber Line) modem, a PSTN (Public Switched Telephone Network) modem, an Ethernet device, a broadband device, a satellite device and/or various other types of wired and/or wireless network communication devices including microwave, radio frequency, infrared, Bluetooth, and near field communication devices. For example, in one implementation, the data vendor server 245 may send asset information comprising various biomedical records, etc., from the database 219, via the network interface 226, to the server 230.

The server 130 (e.g., similar to 130 in FIG. 1) may be housed with the data cloud module 230 (e.g., similar to 230 in FIG. 2A) and its submodules described in FIG. 2A. In some implementations, data cloud module 230 may receive data from database 219 at the data vendor server 245 via the network 260 to generate data analytics. The generated data analytics may also be sent to the user device 210 for review by the user 240 via the network 260.

The database 242 may be stored in a transitory and/or non-transitory memory of the server 130. In one implementation, the database 242 may store data obtained from the data vendor server 245. In one implementation, the database 242 may store parameters of the data cloud model 230. In one implementation, the database 242 may store previously generated data analytics and the corresponding input feature vectors.

In some embodiments, database 242 may be local to the server 130. However, in other embodiments, database 242 may be external to the server 130 and accessible by the server 130, including cloud storage systems and/or databases that are accessible over network 260.

The server 130 includes at least one network interface component 243 adapted to communicate with user device 210 and/or data vendor servers 245, 270 or 280 over network 260. In various embodiments, network interface component 243 may comprise a DSL (e.g., Digital Subscriber Line) modem, a PSTN (Public Switched Telephone Network) modem, an Ethernet device, a broadband device, a satellite device and/or various other types of wired and/or wireless network communication devices including microwave, radio frequency (RF), and infrared (IR) communication devices.

Network 260 may be implemented as a single network or a combination of multiple networks. For example, in various embodiments, network 260 may include the Internet or one or more intranets, landline networks, wireless networks, and/or other appropriate types of networks. Thus, network 260 may correspond to small scale communication networks, such as a private or local area network, or a larger scale network, such as a wide area network or the Internet, accessible by the various components of system 200.

Example System Architecture

Figure 3A:
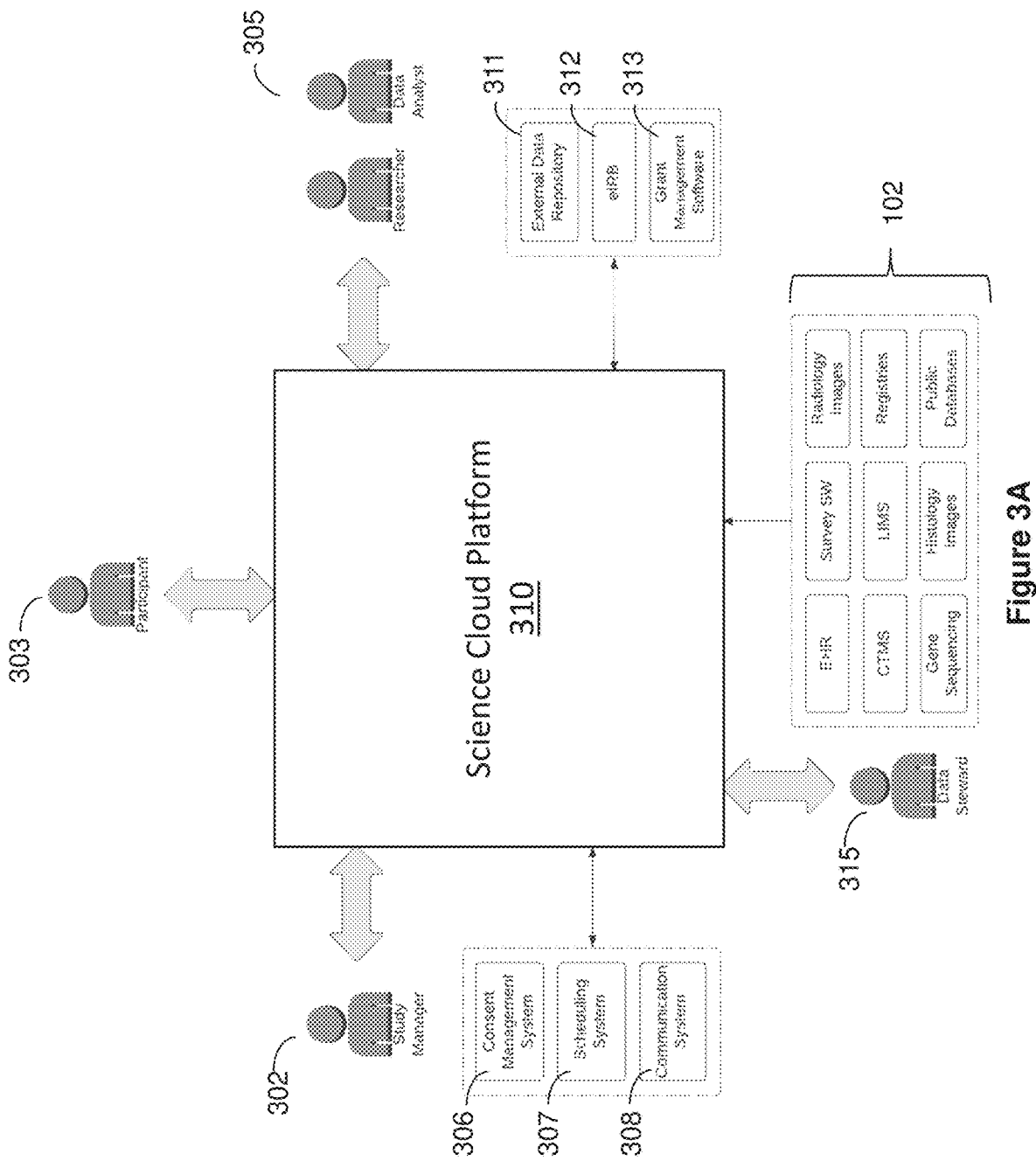
FIG. 3A provides an example architecture of the data cloud platform implemented at the server shown in FIGS. 1 and 3A and interactions with its affiliated entities, according to embodiments described herein.

FIG. 3A provides an example architecture of the data cloud platform implemented at the server 130 shown in FIGS. 1 and 2B and interactions with its affiliated entities, according to embodiments described herein. The data cloud platform 310 (e.g., similar to the data cloud platform 230 in FIGS. 1-2B) may be accessed by and interact with a number of entities, including a study manager 302 who may oversee the research projects), a data steward 315 who may collect and process various raw research data, one or more researchers and data analysts 305 who may obtain processed research data, and other participants 303 such as patients who sign up for a clinical trial, and/or the like.

In one embodiment, the various entities may comprise human personnel. In another embodiment, the various entities may comprise intelligent systems, such as an artificial intelligent agent that performs the duties of a study manager 302, a data steward 315, and/or the like.

In one embodiment, the study manager 302 may interact with the data cloud platform 310 through a consent management system 306 that provides digital consent management with participants (patients) 303, a scheduling system 307 that schedules appointment or engagement with participants, a communication system 308 with participants. For example, in one embodiment, the consent management system 306, scheduling system 307 and the communication system 308 may be part of the applications 216 implemented on a user device 210, which is operated by a study manager user 240 shown in FIG. 2B.

In one embodiment, the data steward 315 may interact with the data cloud platform 310 to facilitate the receipt of various raw research data 102 from various data sources 103*a-n* as shown in FIG. 1. The raw research data 102 may include electronic health record (EHR), health surveys, radiology images, CTMS reports, lab information management system (LIMS) reports, registries, gene sequencing data, histology images, patient information from public databases, and/or the like. For example, in one implementation, the data steward 315 may operate a user device 210 shown in FIG. 2B that implements a data steward application.

In one embodiment, the researcher or data analyst 305 may receive processed research data from the data cloud platform and store such data in an external data repository 311. For example, the researcher or data analyst 305 may operate a user device 210 shown in FIG. 2B, which implements the external data repository 311, an eIRB system 312, and additional research grant software 313.

In one embodiment, a participant (such as a patient) 303 may operate a user device 210 shown in FIG. 2B to manage their own patient portal.

Figure 3B:
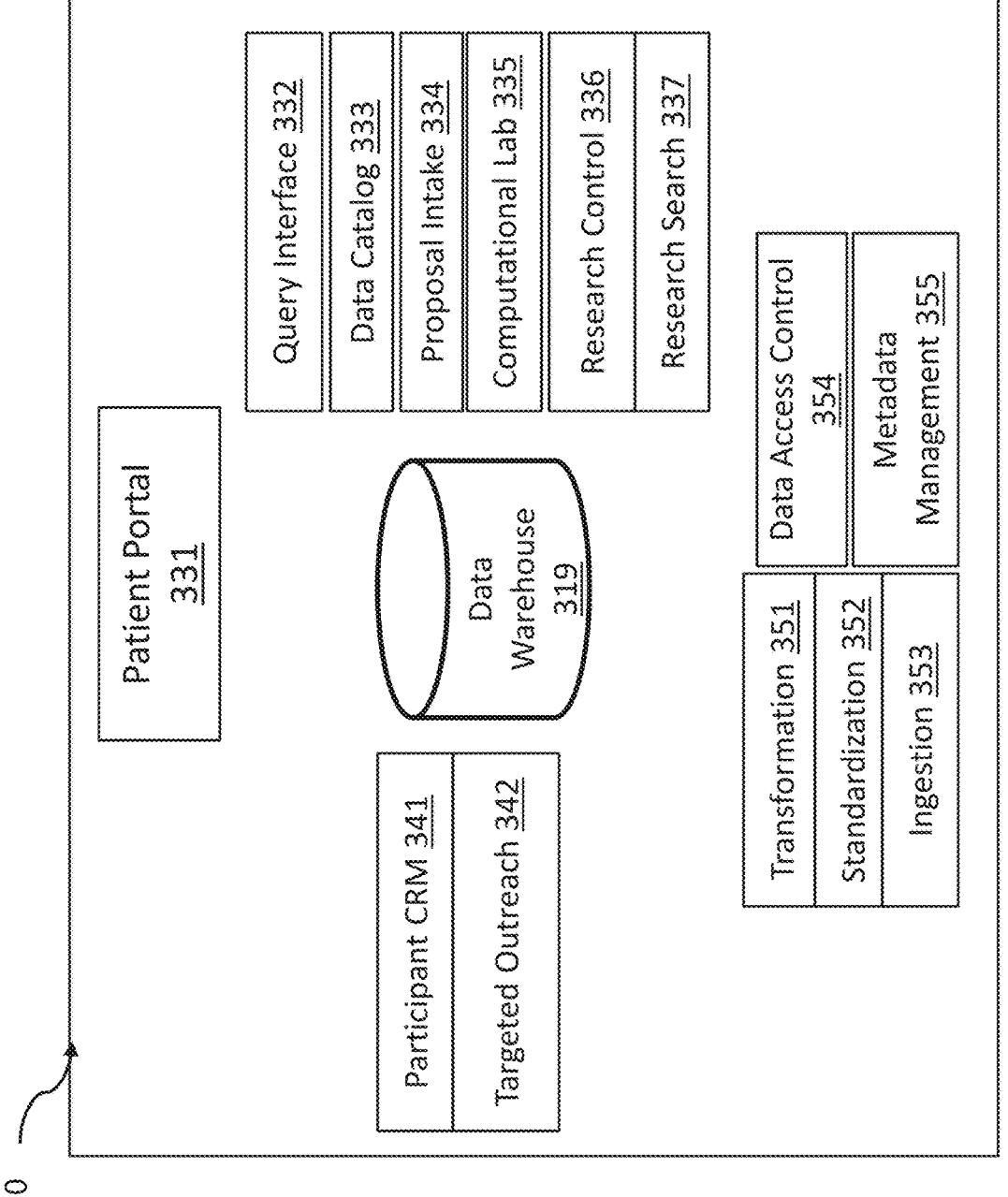
FIG. 3B provides a detailed view of the data cloud platform shown in FIG. 3A, according to embodiments described herein.

FIG. 3B provides a detailed view of the data cloud platform 310, according to embodiments described herein. The data cloud platform 310 may host a variety of applications for different users. For example, the data cloud platform 310 may host a patient portal 331 such that patients 303 may submit patient information and retrieve medical data. The data cloud platform 310 may further host a participant client-relationship management (CRM) application 341 and/or a targeted outreach application 342 for the study manager 302 to manage the patient enrollment and participation. The data cloud platform 310 may further host various interfaces and/or applications for the researchers 305, such as a query interface 332 to submit a research query, a data catalog 333 that displays a list of available research data, a proposal intake platform 334 to intake research proposals, a computational lab application 335 to run lab simulations, a research control application 336, a research search interface 337, and/or the like. Example user interfaces of the various applications 332-337 may be provided in FIGS. 8A-8F.

The data cloud platform 310 may further host various applications for intaking raw research data 102. For example, an ingestion module 353 may receive and ingest various forms of raw data 102, as described in FIG. 3A. A standardization module 352 may convert various data formats into a standardized form, e.g., by scanning and performing OCRs on scanned images of medical records to extract data fields, etc. A transformation module 351 may transform extracted information into a pre-defined format, e.g., the data to be a certain format of "mm-dd-yyyy," the medical service code according to a unified code system, and/or the like. A data access control module 354 and a metadata management module 355 may be operated by the data steward 315 to manage data intake.

Figure 4:
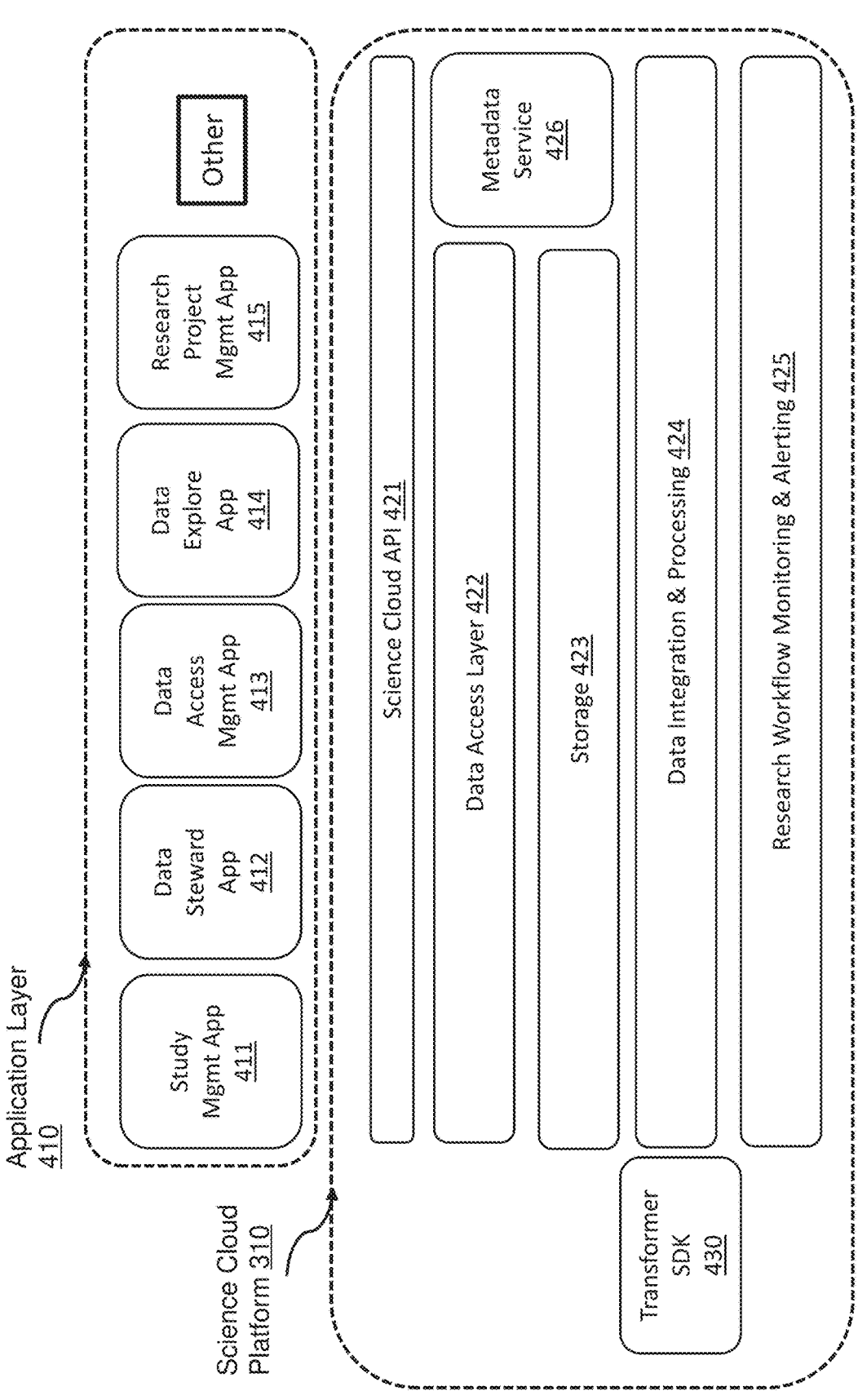
FIG. 4 is an example block diagram illustrating an example application architecture of the data cloud platform described in FIGS. 3A-3B, according to embodiments described herein.

FIG. 4 is an example block diagram illustrating an example application architecture of the data cloud platform 310 described in FIGS. 3A-3B, according to embodiments described herein. For example, the science data cloud platform 310 may be built upon various software and/or hardware components including an observability, logging, monitoring, alerting function module 426, a data ingestion and processing module 425, a storage 423, metadata services 424 and a data access layer 422. The science data cloud platform 310 may further comprise a cloud application programming interface (API) 421 that interfaces with the application layer 410. The application layer 410 in turn supports various applications such as the study management application 411, data steward application 412, data access management application 413, data exploration application 414, research project management application 415, and/or other applications.

In one implementation, the data cloud platform 310 may further provide a transformer software development kit (SDK) 430 such that developers may adapt, change or define data requirements, formats or transformation rules for data transformation.

Example Logic Flows

FIG. 5 is an example logic flow diagram illustrating a method of data integration for managing research project workflow dynamics based on the data cloud platform 230 shown in FIGS. 1-2B and 310 in FIGS. 3A-4, according to some embodiments described herein. One or more of the processes of method 500 may be implemented, at least in part, in the form of executable code stored on non-transitory, tangible, machine-readable media that when run by one or more processors may cause the one or more processors to perform one or more of the processes. In some embodiments, method 500 corresponds to the operation of the data cloud module 230 (e.g., FIGS. 1-2B) and/or the science cloud 310 in FIGS. 3A-4.

As illustrated, the method 500 includes a number of enumerated steps, but aspects of the method 500 may include additional steps before, after, and in between the enumerated steps. In some respects, one or more of the enumerated steps may be omitted or performed in a different order.

At step 502, unstructured data (e.g., 102 in FIG. 1) may be received, via a data interface, from one or more medical data sources (e.g., 103*a-n* in FIG. 1). For example, the unstructured data comprises any combination of raw patient records, research lab journal entries, medical images, and research papers.

At step 504, the unstructured data may be converted, e.g., via the standardization application 352 and the transformation application 351 in FIG. 3B, into a plurality of data samples associated with a set of data attributes according to a pre-defined format. For example, information elements may be extracted from the unstructured data and categorized into the set of data attributes such as patient gender, patient age, patient race, patient residence history, and patient medical history.

At step 506, a training dataset may then be formulated by grouping the plurality of data samples based on past research results. For example, the categorized extracted information elements may then be organized in a form of a spreadsheet having a number of columns representing the set of data attributes and a number of rows representing a patient or a research topic. The research topic may be obtained from past research results indicating the achievability of a type of research findings that are derived from the plurality of data samples.

At step 508, a machine learning engine may be employed to generate predicted research finding achievability based on availability of the set of data attributes in the training dataset. For example, depending on the columns of available data attributes of biomedical research data, the machine learning engine may predict whether these columns of data are sufficient to conduct a particular research topic, e.g., "is there correlation between starting age of smoking and lung cancer before the age of 50?" The machine learning engine may generate a predicted probability, e.g., 55.3% likelihood that the current data is sufficient, 43.2% likelihood that the current data is insufficient, and 1.5% likelihood that the system is unable to predict.

At step 510, the machine learning engine may then be trained based on a training objective that is computed by comparing the predicted research finding achievability and the past research results. For example, training objective may be computed as the cross-entropy loss between a predicted distribution of whether the research finding is achievable and the actual ground-truth achievability of research finding from past research results. The machine learning engine may then be updated by the cross-entropy loss via backpropagation.

At step 512, the trained machine learning engine may then be used to generate a prediction of research findings based on availability of the plurality of data samples in response to research data queries. Additional details of research finding achievability prediction can be found in FIGS. 6-7.

FIG. 6 is an example logic flow diagram illustrating a method of responding to a user query relation to a research topic, according to some embodiments described herein. One or more of the processes of method 600 may be implemented, at least in part, in the form of executable code stored on non-transitory, tangible, machine-readable media that when run by one or more processors may cause the one or more processors to perform one or more of the processes. In some embodiments, method 600 corresponds to the operation of the data cloud module 230 (e.g., FIGS. 1-2B) and/or the science cloud 310 in FIGS. 3A-4.

As illustrated, the method 600 includes a number of enumerated steps, but aspects of the method 600 may include additional steps before, after, and in between the enumerated steps. In some respects, one or more of the enumerated steps may be omitted or performed in a different order.

At step 602, a user query relating to a particular research finding, may be received, via a user interface. For example, the user query may comprise a question asking whether the data platform is able to provide sufficient data to support a particular research topic. For example, the particular research finding may include a correlation between a first data attribute to a second data attribute, and/or a causality between a first data attribute to a second data attribute.

At step 604, the trained machine learning engine may then determine whether the particular research finding is achievable based on an availability of the plurality of data samples and the set of data attributes. For example, the trained machine learning engine may generate a prediction, based on the available data at the data cloud platform, whether the research topic of "correlation between starting age of smoking and lung cancer before the age of 50" is achievable. The prediction from the trained machine learning engine may take a form of a probability distribution, e.g., 55.3% likelihood that the desired correlation finding may be achieved (e.g., whether there is enough research data to tell whether there is or there is no correlation), 43.2% likelihood that is not achievable (e.g., the data is insufficient to tell whether there is or there is no correlation), and 1.5% likelihood that the system is unable to predict.

At step 606, if it is determined that the particular research finding is achievable, method 606 may proceed to step 610, at which a subset of data samples and a subset of data attributes for building the particular research finding may be provided, via the user interface. For example, the data cloud platform may provide a previously obtained and available dataset containing patient smoking history and medical history for this particular research topic.

At step 612, the cloud platform may optionally generate, via a rule-based recommendation engine, a recommendation of workflow steps following the prediction of research findings. For example, workflow steps may include steps to comply with patient consent, privacy requirement to use the data for clinical study, data harvesting process that compliant with regulation, and/or the like.

In another embodiment, at step 606, if it is determined that the particular research finding is not achievable, method 606 may proceed to step 609, where the machine learning engine may optionally generate a recommendation of one or more supplemental data samples or supplemental data attributes. For example, for the particular research topic of "correlation between starting age of smoking and lung cancer before the age of 50," while the data platform may provide a dataset containing patient smoking history and medical history, the machine learning engine may further recommend additional dataset(s) comprising other patient survey data relating to patient diet and lifestyle information.

At step 611, the machine learning engine may further generate a recommendation of one or more data sources for obtaining the supplemental data samples and supplemental data attributes.

FIG. 7 is an example logic flow diagram illustrating an alternative embodiment of responding to a user query relation to a research topic, according to some embodiments described herein. One or more of the processes of method 700 may be implemented, at least in part, in the form of executable code stored on non-transitory, tangible, machine-readable media that when run by one or more processors may cause the one or more processors to perform one or more of the processes. In some embodiments, method 700 corresponds to the operation of the data cloud module 230 (e.g., FIGS. 1-2B) and/or the science cloud 310 in FIGS. 3A-4.

As illustrated, the method 700 includes a number of enumerated steps, but aspects of the method 700 may include additional steps before, after, and in between the enumerated steps. In some respects, one or more of the enumerated steps may be omitted or performed in a different order.

At step 702, the cloud platform may receive, via a user interface, a user query relating to a particular research finding and one or more data samples having one or more data attributes. For example, the cloud platform may receive a research topic of "correlation between starting age of smoking and lung cancer before the age of 50," a first dataset of patient smoking history between ages 20-30, and a second dataset of patient chest radiography images between ages 20-30.

At step 704, the trained machine learning engine may determine whether the one or more data samples are sufficient to establish the particular research finding. For example, the machine learning engine may generate a prediction that the provided datasets may not be sufficient to establish any correlation between starting age of smoking and lung cancer before the age of 50.

At step 706, if it is determined that the one or more data samples are insufficient to establish the particular research finding, method 700 proceeds to steps 709 and/or 711. For example, at step 709, the data cloud platform may provide a recommendation of supplemental data samples from the plurality of data samples in the available data. For another example, at step 711, the data cloud platform may determine an achievable research finding that may be achieved based on an input of the one or more data samples. For example, given the input of a first dataset of patient smoking history between ages 20-30, and a second dataset of patient chest radiography images between ages 20-30, the machine learning engine may determine a high likelihood (e.g., >72.3%) that these datasets are insufficient to achieve a research result indicating whether there is or there is no correlation between starting age of smoking and lung cancer before the age of 50. In that case, the machine learning engine may additionally predict, based on the input of available first dataset and second dataset, the first dataset and the second dataset may be sufficient to conduct a different research topic, e.g., whether there is correlation between a first abnormal chest x-ray result and chronical smoking habit.

At step 706, if it is determined that the one or more data samples are sufficient to establish the particular research finding, method 700 optionally proceeds to steps 710 and/or 712. For example, at step 710, the machine learning engine may generate a research showcase result that is derived from the one or more data samples, e.g., a correlation graph illustrating the correlation between the data attributes. For another example, the machine learning engine may optionally generate (e.g., by a ruled based recommendation) a recommendation of workflow steps following the prediction of research findings.

Example UI Diagrams

FIGS. 8A-8G provide various example user interface (UI) diagrams of the data cloud platform shown in FIGS. 1-4, according to embodiments described herein. The UI diagrams may be displayed on a user device (e.g., 210 in FIG. 2B) operated by any user such as a study manager 302 or the research/data analyst 305 in FIG. 3A.

Figure 8A:
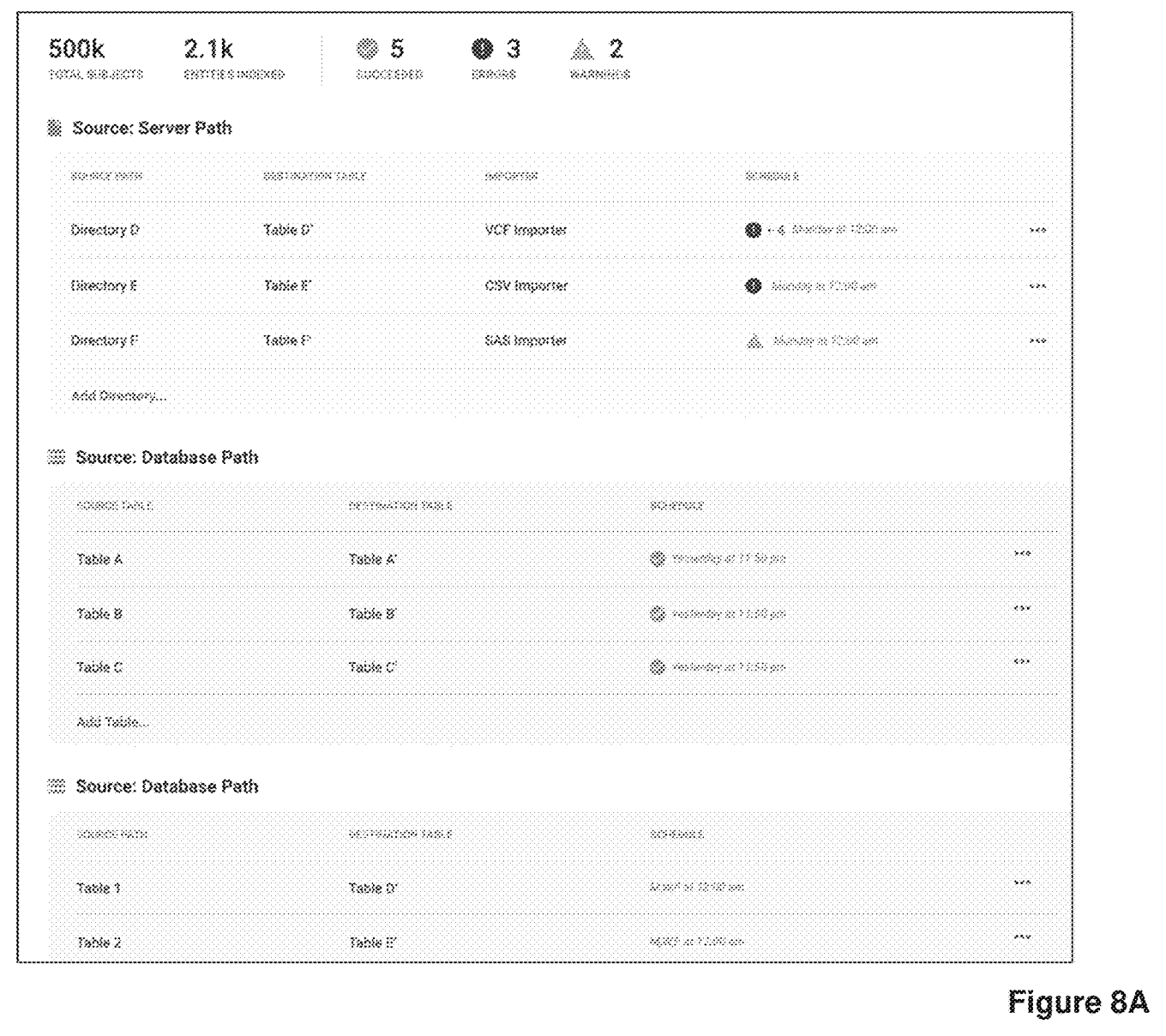
Figure 8B:
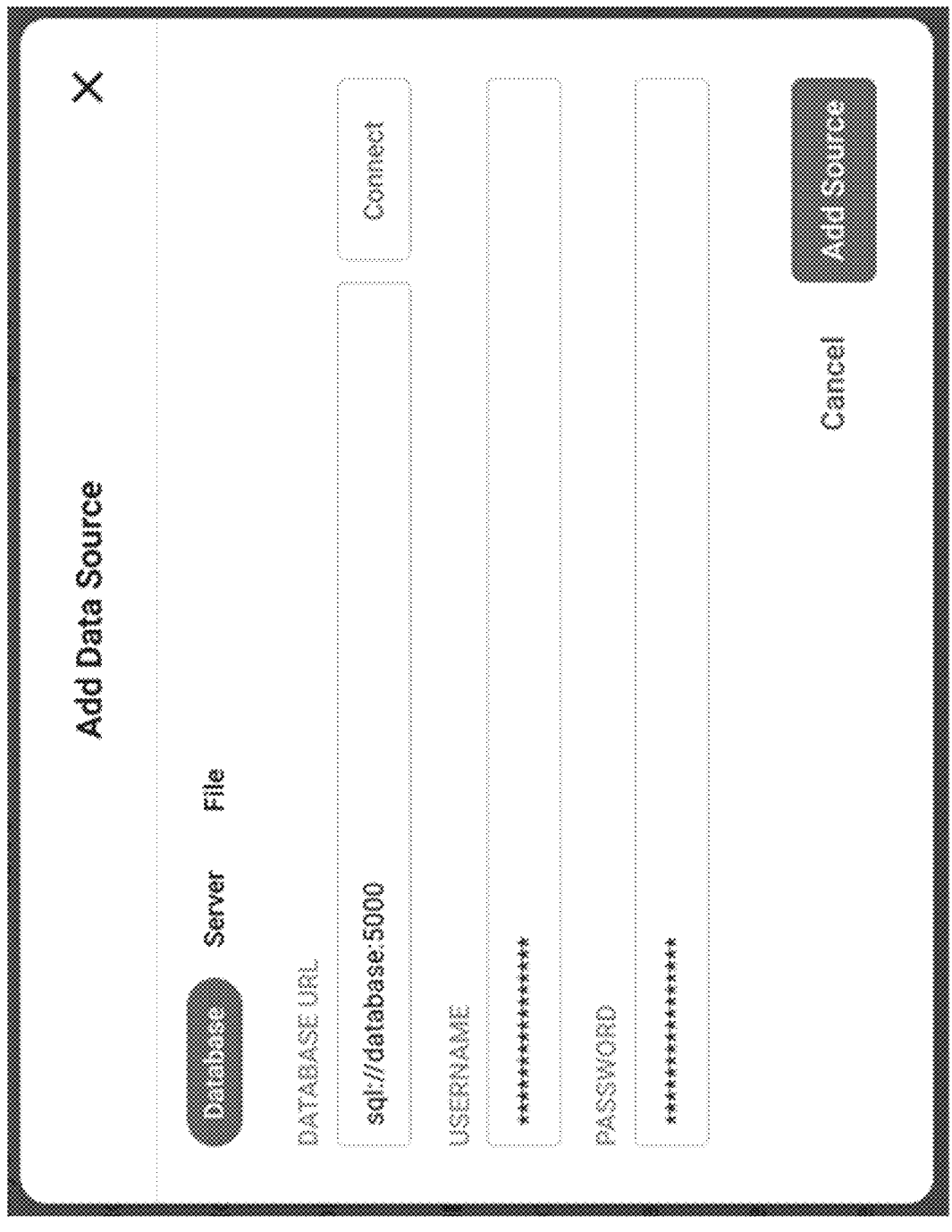
Figure 8D:
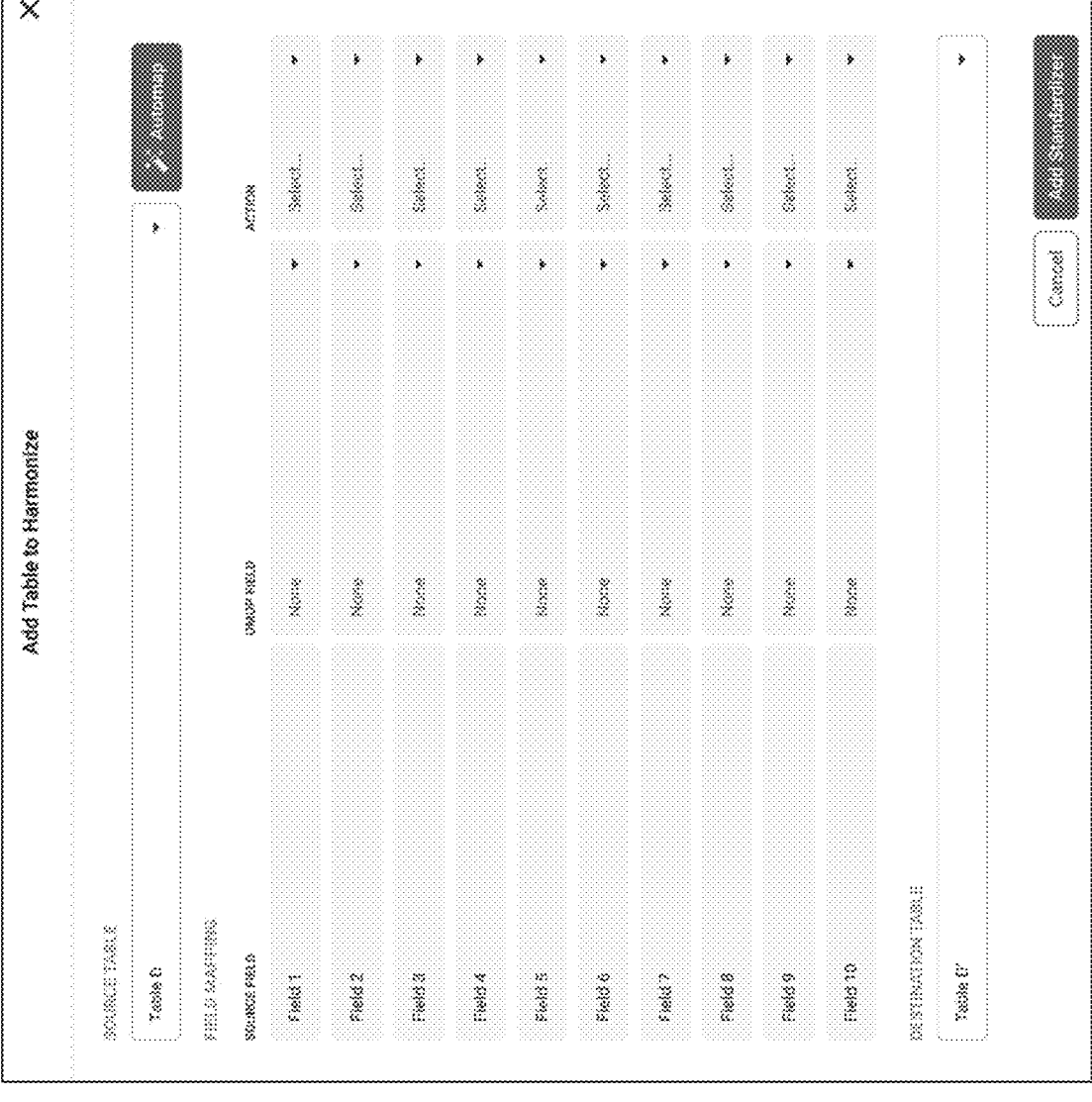
Figure 8E:
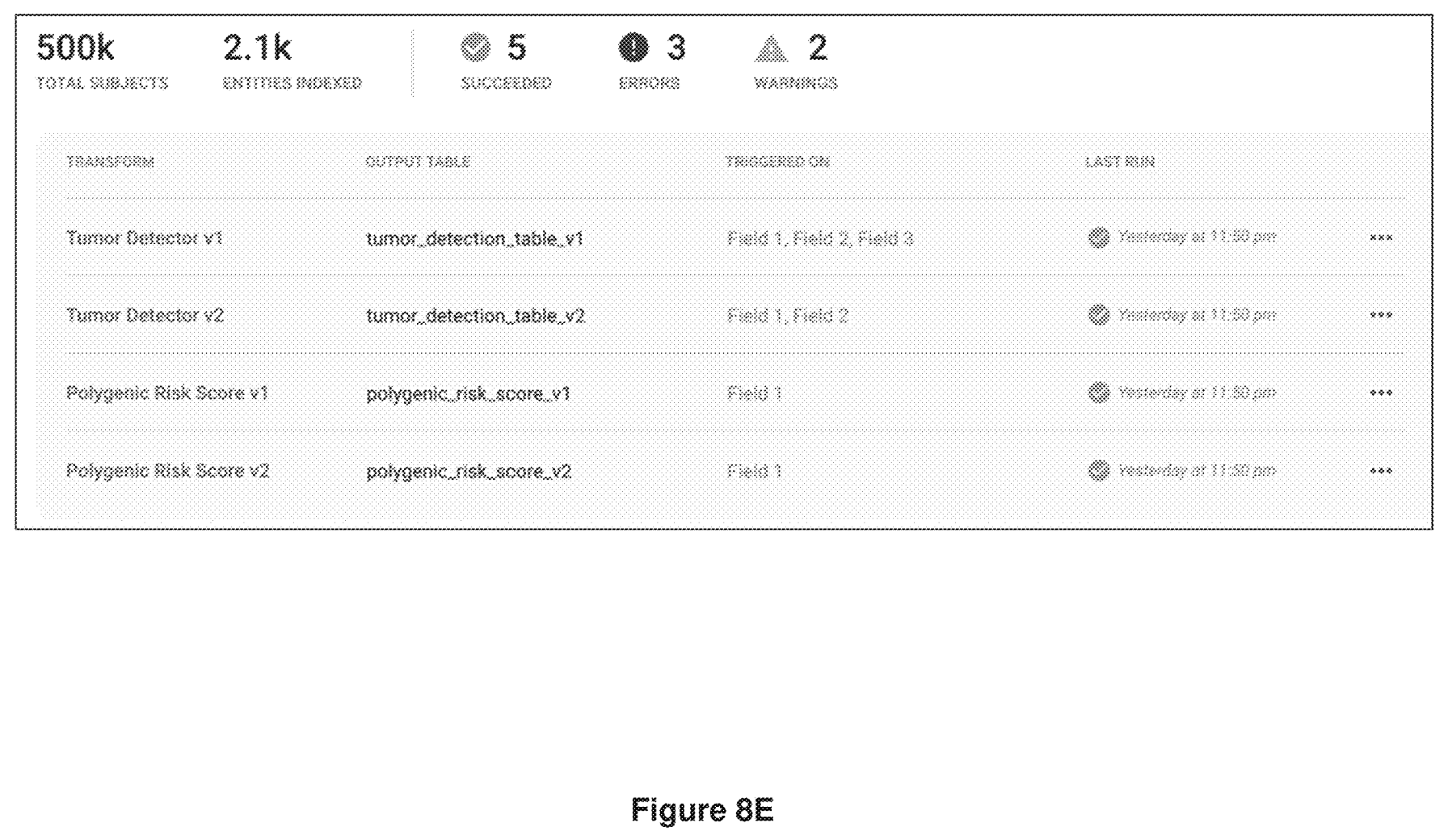
Figure 8G:
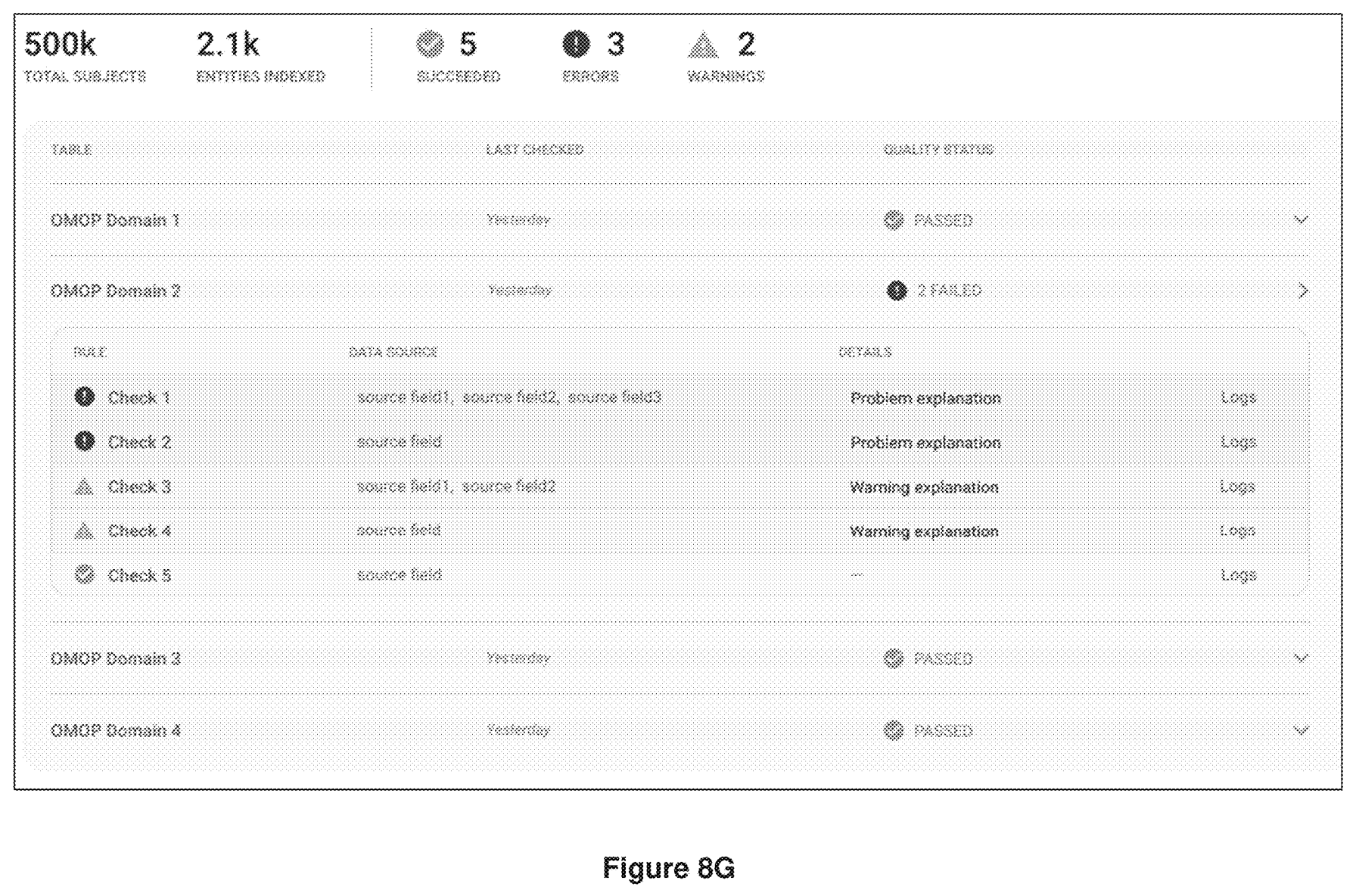

In FIG. 8A, a user may view a data ingest page f data intake, and a list of data sources. In FIG. 8B, a user may add a data source, e.g., by identifying a link such as an URL to the database, and login credentials for access to the database. In FIG. 8C, a user may view a data harmonization page of different data tables. In FIG. 8D, a user may add a new table to the harmonization, and data fields in the new data table may be mapped to the harmonized data fields. In FIG. 8E, a user may view a data transform page of different input documents that are transformed to output tables. In FIG. 8F, a user may add a transform of a new data format. In FIG. 8G, a user may view the quality check summary of data from different domains.

Figure 9A:
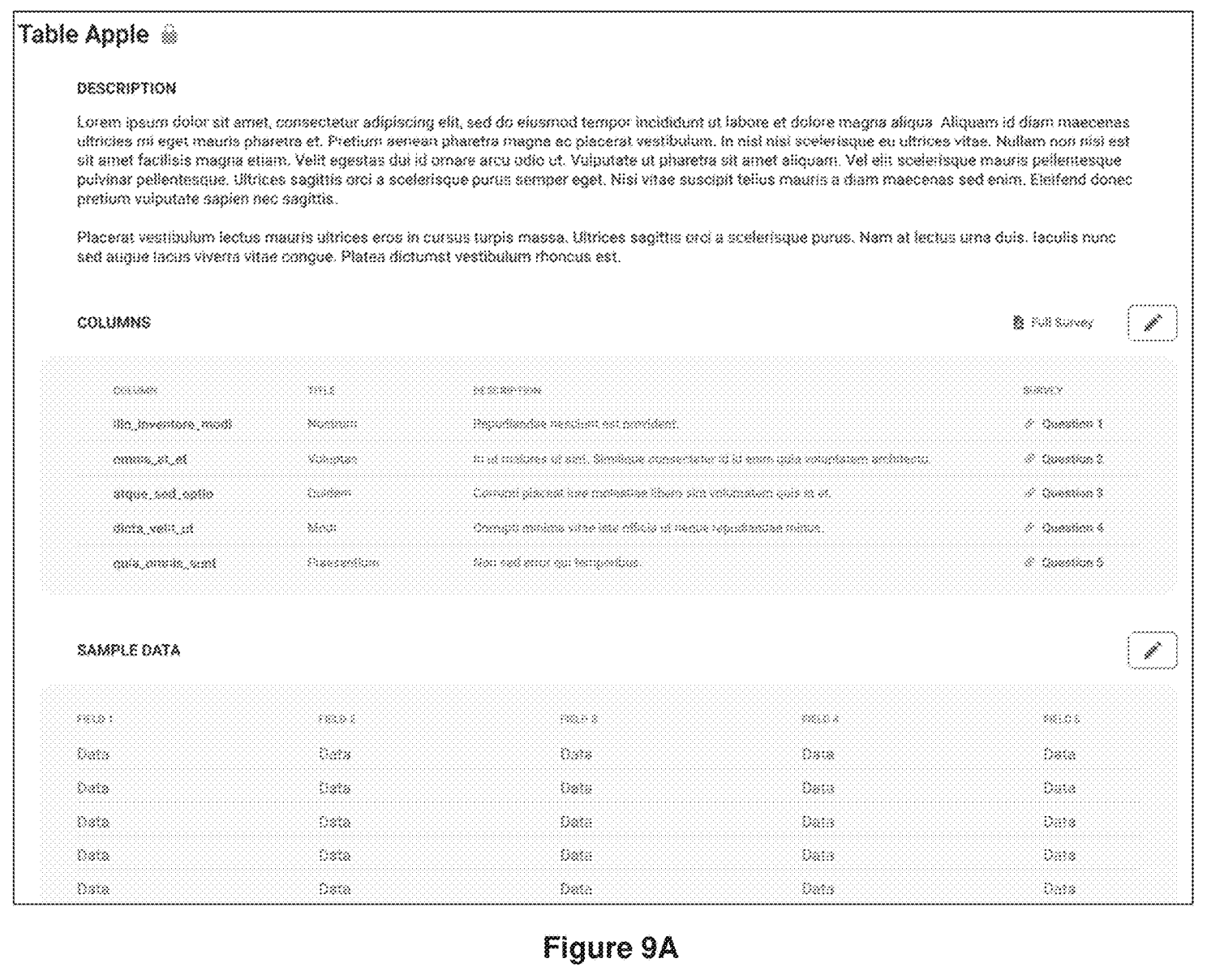
Figure 9B:
Figure 9C:
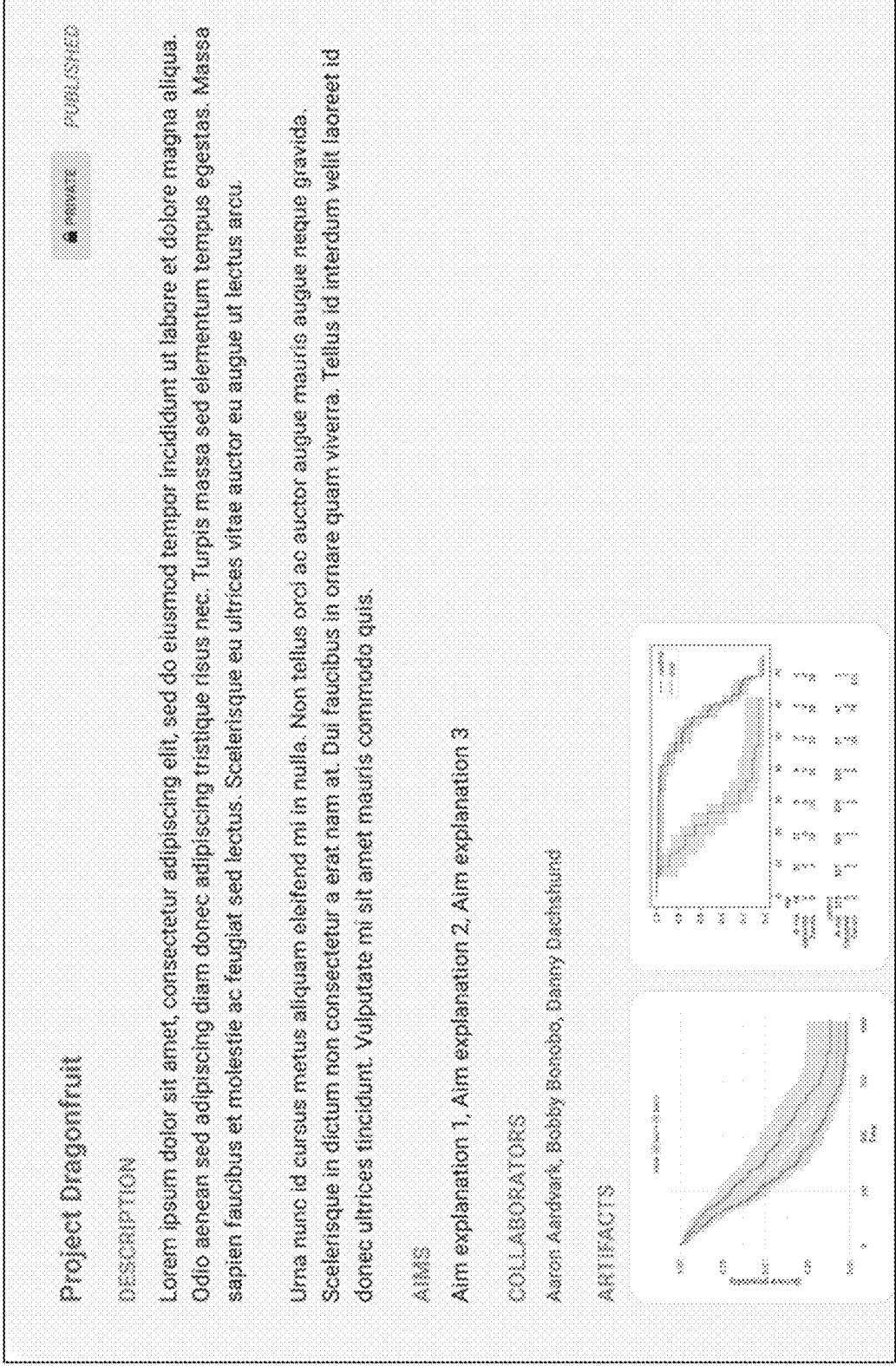
Figure 9E:
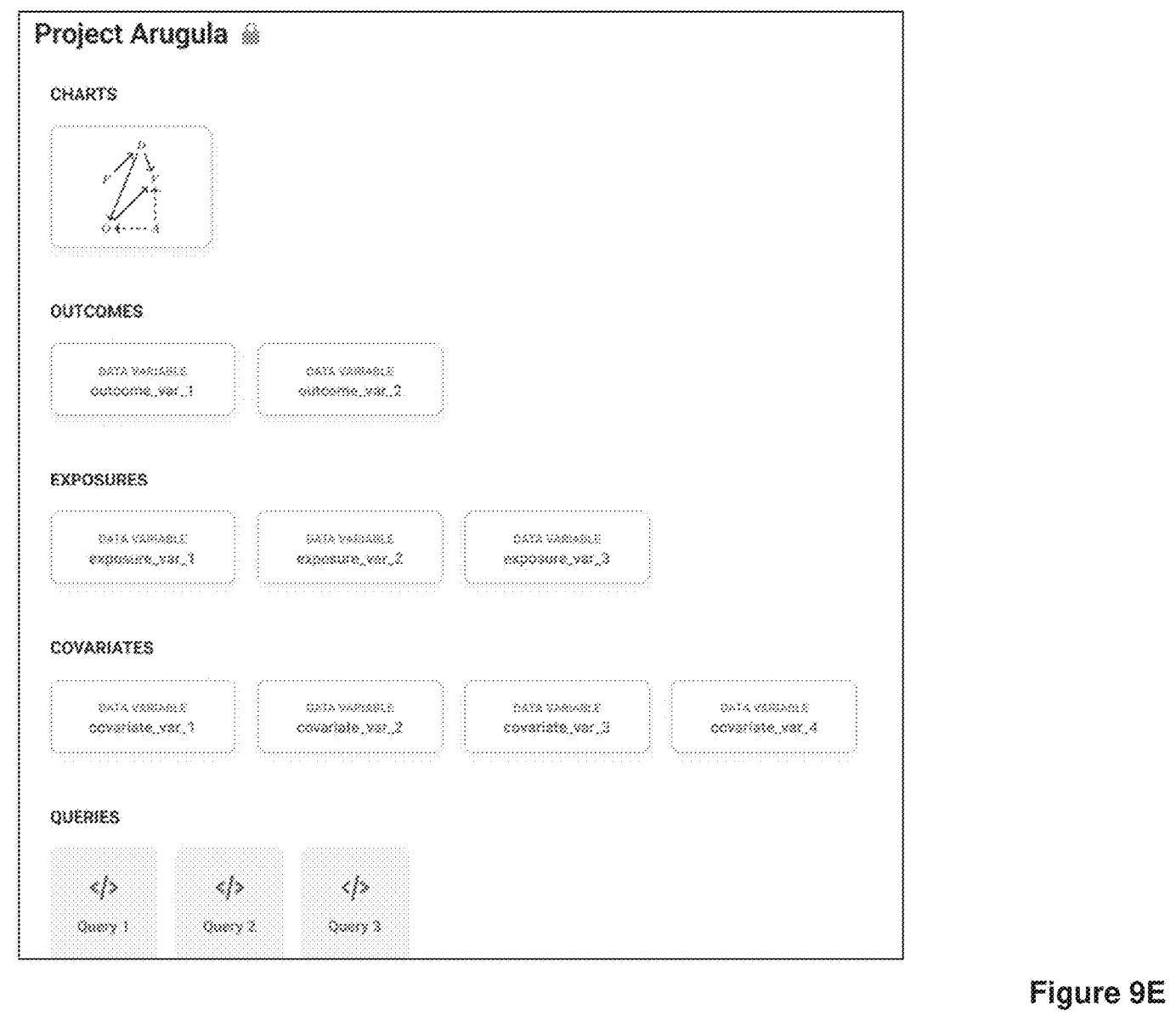

FIGS. 9A-9E provide additional user interface (UI) diagrams of the data cloud platform shown in FIGS. 1-4, according to embodiments described herein. In FIG. 9A, a user may view a summary of data table. In FIG. 9B, a user may view a list of research projects and a brief description. In FIG. 9C, a user may view an example published summary of a particular project. In FIG. 9D, a user may see the timeline overview of a research project for project management. In FIG. 9E, a user may view the example resources for the project.

This description and the accompanying drawings that illustrate inventive aspects, embodiments, implementations, or applications should not be taken as limiting. Various mechanical, compositional, structural, electrical, and operational changes may be made without departing from the spirit and scope of this description and the claims. In some instances, well-known circuits, structures, or techniques have not been shown or described in detail in order not to obscure the embodiments of this disclosure. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Although illustrative embodiments have been shown and described, a wide range of modification, change and substitution is contemplated in the foregoing disclosure and in some instances, some features of the embodiments may be employed without a corresponding use of other features.

One of ordinary skill in the art would recognize many variations, alternatives, and modifications. Thus, the scope of the invention should be limited only by the following claims, and it is appropriate that the claims be construed broadly and, in a manner, consistent with the scope of the embodiments disclosed herein.

What is claimed is:

1. A method of operating a biomedical research data pipeline for managing research project workflow dynamics, the method comprising:

receiving, via a data interface, unstructured data from one or more medical data source(s) and a user query relating to a research topic;

converting the unstructured data into a plurality of data samples, each having a set of data attributes according to a pre-defined format;

formulating a training dataset by grouping the plurality of data samples based on past research results;

determining that the research topic relates to a first data attribute and a second data attribute from the set of data attributes;

generating, by the machine learning engine, a predicted research finding achievability indicating whether the research topic is achievable based on an availability of at least the first data attribute and the second attribute from the set of data attributes in the training dataset;

training the machine learning engine based on a training objective that is computed by comparing the predicted research finding achievability and past research results indicating whether the availability of the at least the first data attribute and the second attribute is sufficient to achieve the research topic; and generating, by the trained machine learning engine, a prediction of achievable research findings based on an availability of the plurality of data samples in response to research data queries, the prediction including a probability indicating a likelihood of whether the plurality of data samples is sufficient or insufficient to achieve one or more desired research findings.

2. The method of claim 1, wherein the unstructured data comprises any combination of:

raw patient records;

research lab journal entries;

medical images; and research papers.

3. The method of claim 1, wherein the converting the unstructured data into the plurality of data samples comprises:

extracting information elements from the unstructured data;

categorizing the extracted information elements into the set of data attributes; and organizing the categorized extracted information elements in a form of a spreadsheet having a number of columns representing the set of data attributes and a number of rows representing a patient or a research topic.

4. The method of claim 1, wherein each data sample from the plurality of data samples comprises any of: patient gender, patient age, patient race, patient residence history, and patient medical history; and wherein the past results include an achievability of a type of research findings that are derived from the plurality of data samples.

5. The method of claim 1, further comprising:

receiving, via a user interface, a user query relating to a particular research finding;

US 12,632,790 B1

15 determining, by the trained machine learning engine, whether the particular research finding is achievable based on the availability of the plurality of data samples and the set of data attributes;

in response to determining that the particular research finding is achievable, providing, via the user interface, a subset of data samples and a subset of data attributes for building the particular research finding.

6. The method of claim 5, further comprising:

in response to determining that the particular research finding is unachievable, generating a recommendation of one or more supplemental data samples or supplemental data attributes and a recommendation of one or more data sources for obtaining the supplemental data samples and supplemental data attributes.

7. The method of claim 1, further comprising:

receiving, via a user interface, a user query relating to a particular research finding and one or more data samples having one or more data attributes; and determining, by the trained machine learning engine, whether the one or more data samples are sufficient to establish the particular research finding.

8. The method of claim 7, further comprising:

in response to determining that the one or more data samples are insufficient to establish the particular research finding, providing a recommendation of supplemental data samples from the plurality of data samples.

9. The method of claim 7, further comprising:

in response to determining that the one or more data samples are insufficient to establish the particular research finding, determining, by the trained machine learning engine, an achievable research finding based on an input of the one or more data samples.

10. The method of claim 1, wherein the prediction of research findings comprises:

an achievability prediction indicating whether a particular research finding is achievable given the availability of the plurality of data samples; and a research showcase result that is derived from a reduced set from the plurality of data samples when the achievability prediction indicates that the particular research finding is achievable.

11. The method of claim 1, wherein the prediction of research finding comprises any of:

a correlation between a first data attribute to a second data attribute; and a causality between a first data attribute to a second data attribute.

12. The method of claim 1, further comprising:

generating, via a rule-based recommendation engine, a recommendation of workflow steps following the prediction of research findings.

13. A system of operating a biomedical research data pipeline for managing research project workflow dynamics, the system comprising:

a communication interface that receives unstructured data from one or more medical data sources and a user query relating to a research topic;

a memory storing parameters of a machine learning engine and a plurality of processor-executable instructions; and one or more processors that read and execute the plurality of processor-executable instructions to perform operations comprising:

converting the unstructured data into a plurality of data samples, each having a set of data attributes according to a pre-defined format;

formulating a training dataset by grouping the plurality of data samples based on past research results;

determining that the research topic relates to a first data attribute and a second data attribute from the set of data attributes;

generating, by the machine learning engine, predicted research finding achievability indicating whether the research topic is achievable based on an availability of the set of data attributes in the training dataset;

training the machine learning engine based on a training objective that is computed by comparing the predicted research finding achievability and past research results indicating whether the availability of the at least the first data attribute and the second attribute is sufficient to achieve the research topic; and generating, by the trained machine learning engine, a prediction of achievable research findings based on an availability of the plurality of data samples in response to research data queries, the prediction including a probability indicating a likelihood of whether the plurality of data samples is sufficient or insufficient to achieve one or more desired research findings.

14. The system of claim 13, wherein the operations further comprise:

receiving, via a user interface, a user query relating to a particular research finding;

determining, by the trained machine learning engine, whether the particular research finding is achievable based on the availability of the plurality of data samples and the set of data attributes;

in response to determining that the particular research finding is achievable, providing, via the user interface, a subset of data samples and a subset of data attributes for building the particular research finding; and in response to determining that the particular research finding is unachievable, generating a recommendation of one or more supplemental data samples or supplemental data attributes and a recommendation of one or more data sources for obtaining the supplemental data samples and supplemental data attributes.

15. The system of claim 13, wherein the operations further comprise:

receiving, via a user interface, a user query relating to a particular research finding and one or more data samples having one or more data attributes;

determining, by the trained machine learning engine, whether the one or more data samples are sufficient to establish the particular research finding; and in response to determining that the one or more data samples are insufficient to establish the particular research finding, providing a recommendation of supplemental data samples from the plurality of data samples.

16. The system of claim 15, wherein the operations further comprise:

in response to determining that the one or more data samples are insufficient to establish the particular research finding, determining, by the trained machine learning engine, an achievable research finding based on an input of the one or more data samples.

17. The system of claim 13, wherein the prediction of research findings comprises:

an achievability prediction indicating whether a particular research finding is achievable given the availability of the plurality of data samples; and a research showcase result that is derived from a reduced set from the plurality of data samples when the achievability prediction indicates that the particular research finding is achievable.

18. The system of claim 13, wherein the prediction of research finding comprises any of:

a correlation between a first data attribute to a second data attribute; and a causality between a first data attribute to a second data attribute.

19. The system of claim 13, wherein the operations further comprise:

generating, via a rule-based recommendation engine, a recommendation of workflow steps following the prediction of research findings.

20. A non-transitory processor-readable storage medium storing a plurality of processor-executable instructions for operating a biomedical research data pipeline for managing research project workflow dynamics, the instructions being executed by one or more processors to perform operations comprising:

receiving, via a data interface, unstructured data from one or more medical data sources and a user query relating to a research topic;

converting the unstructured data into a plurality of data samples, each having a set of data attributes according to a pre-defined format;

formulating a training dataset by grouping the plurality of data samples based on past research results;

determining that the research topic relates to a first data attribute and a second data attribute from the set of data attributes;

generating, by the machine learning engine, a predicted research finding achievability indicating whether the research topic is achievable based on an availability of at least the first data attribute and the second attribute from the set of data attributes in the training dataset;

training the machine learning engine based on a training objective that is computed by comparing the predicted research finding achievability and past research results indicating whether the availability of the at least the first data attribute and the second attribute is sufficient to achieve the research topic; and generating, by the trained machine learning engine, a prediction of achievable research findings based on an availability of the plurality of data samples in response to research data queries, the prediction including a probability indicating a likelihood of whether the plurality of data samples is sufficient or insufficient to achieve one or more desired research findings.

* * * * *